US005229292A

United States Patent [19]

Stock et al.

[11] Patent Number: 5,229,292

[45] Date of Patent: Jul. 20, 1993

[54] BIOLOGICAL CONTROL OF INSECTS USING PSEUDOMONAS STRAINS TRANSFORMED WITH *BACILLUS THURINGIENSIS* INSECT TOXINGENE

[75] Inventors: Carolyn A. Stock, Monona; Thomas J. McLoughlin, Cottage Grove; Janet A. Klein; Michael J. Adang, both of Madison, all of Wis.

[73] Assignee: Stine Seed Farm, Inc., Adel, Iowa

[21] Appl. No.: 891,305

[22] Filed: Jul. 28, 1986

[51] Int. Cl.[5] ........................ C12N 1/21; A01N 63/00

[52] U.S. Cl. ............................ 435/252.34; 424/93 N

[58] Field of Search ............. 435/93, 68, 172.3, 172.1, 435/91, 252.74, 170, 171, 253, 254, 320, 849, 911, 69.1, 71.2, 172.5, 252.34, 320.1, 874; 436/83; 935/6, 9, 10, 22, 32, 33, 59, 60, 61, 62, 849, 911

[56] References Cited

U.S. PATENT DOCUMENTS

| | | | |
|---|---|---|---|
| 4,448,885 | 5/1984 | Schnepf et al. | 435/252.33 |
| 4,467,036 | 8/1984 | Schnepf et al. | 435/320.1 |
| 4,588,584 | 5/1986 | Lumsden et al. | 424/93 R |
| 4,652,628 | 3/1987 | Walfield et al. | 530/324 |
| 4,695,455 | 9/1987 | Barnes et al. | 424/93 D |
| 4,771,131 | 9/1988 | Herrnstadt | 536/27 |

FOREIGN PATENT DOCUMENTS 0185005 6/1986 European Pat. Off. .

OTHER PUBLICATIONS

Neilson J. of Bacteriol. 1983 pp. 559-566.

Bergey's Manual of Systematic Bacteriology, vol. 1 Eds. Krieg et al., pp. 141, 162, 165, 174, (1984).

Panopoulos, N. J., 1986, In: Microbiology of the Phyllosphere, N. J. Fokkema and J. Van Den Heuvel (eds), Cambridge Univ Pres, Cambridge, pp. 312-334.

Lindow, S. E., 1986, In: Microbiology of the Phyllosphere, N. J. Fokkema and J. Van Den Heuvel (eds), Cambridge Univ. Press, Cambridge, pp. 293-311.

Kennell, D. E., 1985, In: Maximizing Gene Expression, W. Reznikoff and L. Gold (eds), Butterworth Press, Boston, pp. 101-142.

Goldberg et al., 1985, In: Maximizing Gene Expression, W. Reznikoff and L. Gold (eds), Butterworth Press, Boston, pp. 287-314.

Cullen et al., 1986, Tibtech, pp. 115-119.

Kronstad et al. (1983) J. Bacteriol. 154:419-428.

Whiteley et al.: (1982) In: *Molecular Cloning and Gene Regulation in Bacilli ganesan* et al. (eds.) pp. 131-144.

Adang et al. (1985) Gene 36:289-300.

Thorne et al. (1986) J. Bacteriol. 166:801-811.

Held et al. (1982) Proc. Natl. Acad. Sci. USA 79:6065-6069.

Watrud et al. (1985) In: *Engineered Organism in the Environment: Scientific Issues* Hafbvorson et al. (eds.) American Society of Microbiology Wash. D.C.

Palleroni and Holmes (1981) Int. J. System. Bacteriol. 31:479-481.

*Primary Examiner*—Richard A. Schwartz
*Assistant Examiner*—J. L. LeGuyader
*Attorney, Agent, or Firm*—Greenlee and Winner

[57] ABSTRACT

Methods of biological control of agricultural insect pests are disclosed. These methods utilize biological control agents which are genetically altered strains of root-colonizing strains of members of the species *P. cepacia*. These strains are genetically altered by introduction of genes encoding insect toxic crystal proteins, and are thereby rendered insect toxic. Genetically altered insect toxic bacterial strains are also provided.

17 Claims, 4 Drawing Sheets

BIOLOGICAL CONTROL OF INSECTS USING PSEUDOMONAS STRAINS TRANSFORMED WITH *BACILLUS THURINGIENSIS* INSECT TOXINGENE

FIELD OF THE INVENTION

The present invention relates in general to biological insect control in plants. More particularly it relates to a method of protecting plants from insect pests by inoculating plants or plant parts with strains of *Pseudomonas cepacia*, which are effective plant root or leaf colonizers, which have been genetically altered by introduction of a gene encoding an insect toxic crystal protein from a strain of *Bacillus thuringiensis*. Genetically altered strains of *Pseudomonas cepacia* and insecticidal compositions containing these strains are provided.

BACKGROUND OF THE INVENTION

Gram-positive bacteria of the species *Bacillus thuringiensis* produce proteinaceous crystals that are lethal to a number of insects including agricultural insect pests (Table 1). Reviews are available detailing the microbiology, toxicology and molecular genetics of *Bacillus thuringiensis* including: Sommerville (1973) Ann. N.Y. Acad. Sci. 217:93-103; Rogoff and Yousten (1969) Ann. Rev. Microbiol. 23:357-389; Bulla et al. (1975) Ann. Rev. Microbiol. 29:163-190; Dulmage (1981) in *Microbial Control of Pests and Plant Diseases*, Burges (ed.), Academic Press, London, pp. 193-222; Aronson et al. (1986) Microbiol. Rev. 50:1-24.

A number of subspecies of *Bacillus thuringiensis* (Table 2) have been described which produce crystal proteins toxic to lepidopteran, dipteran or coleopteran insects. The crystals are parasporal, forming during sporulation, within the cell. *Bacillus thuringiensis* varieties display varying spectra of activity. Many subspecies, for example kurstaki strains, are toxic primarily for lepidopterans. The crystals of these subspecies contain a non-toxic protoxin of 130-140 kd molecular weight. This protoxin is solubilized and degraded to a toxic polypeptide (about 68 kd molecular weight) in the midgut of susceptible insects. The protoxin can also be solubilized and activated by protease treatment, in vitro. Several subspecies, particularly israelensis strains, display selective insecticidal activity toward Diptera (i.e., mosquitoes or black flies). Dipteran toxic protein appears to be distinct from the kurastaki crystal protein, having different overall amino acid composition and being immunologically distinct. The major component of crystals of israelensis strains has been reported to be a 26-28 kd protein, a 65 kd protein, or most recently a 130 kd protein (Hurley et al. (1985) Biochem. Biophys. Res. Comm. 126:961-965; Ward et al. (1984) FEBS Lett. 175:377-382; and Armstrong et al. (1985) J. Bacteriol. 161:39-46; Visser et al. (±1986) FEMS Microbiology Let. 33:211-214). The mosquitocidal toxin found in some kurstaki subspecies is reported to be a 65 kd protein (Yamamoto and McLoughlin (1981) Biochem. Biophys. Res. Comm. 103:414-421) and is believed to be distinct from the israelensis mosquitocidal protein. Two *Bacillus thuringiensis* variants (Krieg et al. (1983) Z. Ang. Ent. 96:500-508; Krieg et al. (1984) Ang. Schadlingskde. Pflanzenschutz, Univeltschutz 57:145-150; and Herrnstadt et al. (1986) Biotechnology 4:305-308) have recently been described which display toxicity for Coleoptera rather than Lepidoptera. Crystals of one of these varieties, designated san diego, are reported to have a major protein component of about 64 kd. No higher molecular weight precursor was identified in gels of crystal components; however, an 83 kd protein is reported to be expressed by san diego CP genes cloned in *Escherichia coli*. The coleopteran toxin does not cross react with antiserum raised to lepidopteran specific strains kurstaki HD-1 or HD-73, and there is little peptide homology between the coleopteran toxin and HD-73 protein. It is not as yet known whether protoxins are degraded to produce these toxic proteins in the cases of the dipteran and coleopteran specific toxins.

TABLE 1

Insects susceptible to *B. thuringiensis* insecticidal protein

COLEOPTERA
- *Popilia japonia* (Japanese beetle)
- *Silophilus granarius* (granary weevil)
- *Anthonomus grandis* (boll weevil)
- *Leptinotarsa decemlineata* (Colorado potato beetle)
- *Pyrrhalta luteola* (elm leaf beetle)
- *Diabiotica undecimpunctata* (Western spotted cucumber beetle)
- *Haltica tombacina*
- *Otiorhynchus sulcatus* (black vine weevil)
- *Tenebrio molitor* (yellow mealworm)
- *Agelastica alni* (blue alder leaf beetle)

DIPTERA
- *Aedes aegypti* (yellow-fever mosquito)
- *A. atlanticus*
- *A. cantans*
- *A. capsius*
- *A. cinereus*
- *A. communis*
- *A. detrius*
- *A. dorsalis*
- *A. dupreei*
- *A. melanimon*
- *A. nigromaculis* (pature mosquito)
- *A. punctor*
- *A. sierrens* (western treehole mosquito)
- *A. sollicitans* (brown salt marsh mosquito)
- Aedes sp.
- *A. taeniorhynchus* (black salt marsh mosquito)
- *A. tarsalis*
- *A. tormentor*
- *A. triseriatus*
- *A. vexans* (inland floodwater mosquito)
- *Anopheles crucians*
- *A. freeborni*
- *A. quadrimaculatus* (common malaria mosquito)
- *A. sergentii*
- *A. strephensi*
- Anopheles sp.
- *Chironomus plumosus* (Chironomus: midges, biting)
- Chirnomus sp.
- *C. tummi*
- *Culex erraticus*
- *C. inornata*
- *C. nigripalus*
- *C. peus*
- *C. pipiens* (northern house mosquito)
- *C. quinquefasciatus* (*C. pipiens fatigans*) (southern house mosquito)
- *C. rustuans*
- Culex sp.
- *C. tritaeniorhynchus*

*C. tarsalis* (western encephalitis mosquito)
*C. territans*
*C. univittatus*
*Culiseta incidens* (Culiseta: mosquitos)
*C. inornata*
Diamessa sp.
Dixa sp. (Dixa: midges)
*Eusimulium* (*Simulium*) *latipes* (Eusimlium: gnats)
*Goeldichironomus holoprasinus*
*Haematobia irritans* (horn fly)
*Hippelates collusor*
*Odagima ornata*
*Pales pavida*
Polpomyia sp. (Polpomyia: midges, biting)
Polypedilum sp. (Polypedilum: midges)
*Psorophora ciliata*
*P. columiae* (confinnis) (Florida Glades mosquito, dark rice field mosquito)
*P. ferox*
*Simulium alcocki* (Simulium: black flies)
*S. argus*
*S. cervicornutum*
*S. damnosum*
*S. jenningsi*
*S. piperi*
*S. tescorum*
*S. tuberosum*
*S. unicornutum*
*S. venustum*
*S. verecundum*
*S. vittatum*
*Uranotaenia inguiculata*
*U. lowii*
*Wyeomyia mitchellii* (Wyeomyia: mosquito)
*W. vanduzeei*

HYMENOPTERA
*Athalis rosae* (as colibri)
*Nematus* (*Pteronidea*) *ribesii* (imported currantworm)
*Neodiprion banksianae* (jack-pine fly)
*Priophorus tristis*
*Pristiphora erichsonii* (larch sawfly)

LEPIDOPTERA
*Achaea janta* (croton caterpillar)
*Achrois grisella* (lesser wax moth)
*Achyra rantalis* (garden webworm)
*Acleris variana* (black-headed budworm)
Acrobasis sp.
*Acrolepis alliella*
*Acrolepiopsis* (*Acrolepis*) *assectella* (leek moth)
*Adoxohyes orana* (apple leaf roller)
*Aegeria* (*Sanninoidea*) *exitiosa* (peach tree borer)
*Aglais urticae*
*Agriopsis* (*Erannis*) *aurantiaria* (Erannis: loopers)
*A.* (*E.*) *leucophaearia*
*A. marginria*
*Agrotis ipsilon* (as ypsilon) ( black cutworm)
*A. segetum*
*Alabama argillacea* (cotton leafworm)
*Alsophila aescularis*
*A. pometaria* (fall cankerworm)
*Amorbia essigana*
*Anadevidia* (*Plusia*) *peponis*
*Anisota senatoria* (orange-striped oakworm)
*Anomis flava*
*A.* (*Cosmophila*) *sabulifera*
*Antheraea pernyi*
*Anticarsia gemmatalis* (velvetbean caterpillar)
*Apocheima* (*Biston*) *hispedaria*
*A. pilosaria* (pedaria)
*Aporia cateraegi* (black-veined whitemoth)
*Archips argysopilus* (ugly-nest caterpillar)
*A. cerasivoranus*
*A. crataegana*
*A. podana*
*A.* (*Cacoecia*) *rosana*
*A. xylosteana*
*Artcia caja*
*Argyrotaenia mariana* (gray-banded leaf rollar)
*A. velutinana* (red-banded leaf roller)
*Ascia* (*Pieris*) *monuste oreis*
*Ascotis selenaria*
*Atteva aurea* (alianthus webworm)
*Autographa californica* (alfalfa looper)
*A.* (*Plusia*) *gamma*
*A. nigrisigna*
*Autoplusia egena* (bean lead skeletonizer)
*Azochis gripusalis*
*Bissetia steniella*
*Bombyx mori* (silkworm)
*Brachionycha sphinx*
*Bucculatrix thurberialla* (cotton leaf perforator)
*Bupolus piniarius* (bupolus: looper)
*Cacoecimorpha pronubana*
*Cactoblastis cactorum* (cactus moth)
*Caloptilia* (*gracillaria*) *invariabilis*
*C.* (*G*) *syringella* (lilac leaf miner)
*C.* (*G*) *theivora*
*Canephora asiatica*
*Carponsia niponensis*
Ceramidia sp.
*Cerapteryx graminis*
*Chilo auricilius*
*C. sacchariphagus indicus*
*C. suppressalis* (rice stem borer, Asiatic rice borer)
*Choristoneura fumiferana* (spruce budworm)
*C. murinana* (fir-shoot roller)
*Chrysodeixis* (*plusia*) *chalcites* (green garden looper)
*Clepsos spectrana*
*Cnaphalocrocis medinalis*
*Coleotechnites* (*Recrvaris*) *milleri* (lodgepole needle miner)
*C. nanella*
*Colias eurytheme* (alfalfa caterpiller)
*C. lesbia*
*Colotois pennaria*
*Crambus bonifatellus* (fawn-colored lawn moth, sod webworm)
*C. sperryellus*
Crambus spp.
*Cryptoblabes gnidiella* (Christmas berry webworm)
*Cydia funebrana*
*C.* (*Grapholitha*) *molesta* (oriental fruit moth)
*C.* (*Laspeyresta*) *pomonella* (codling moth)
*Datana integerrima* (walnut caterpillar)
*D. ministra* (yellow-necked caterpillar)
*Dendrolimus pini*
*D. sibiricus*
*Depressaria marcella* (a webworm)
*Desmia funeralis* (grape leaf folder)
*Diachrysia* (*Plusia*) *orichalcea* (a semilooper)
*Diacrisia virginica* (yellow wollybear)
*Diaphania* (*Margaronia*) *indica*
*D. nitidalis* (pickleworm)
*Diaphora mendica*
*Diatraea grandiosella* (southwestern corn borer)
*D. saccharalis* (sugarcane borer)

*Dichomeris marginella* (juniper webworm)
*Drymonia ruficornis* (as chaonia)
Drymonia sp.
*Dryocampa rubicunda* (greenstriped mapleworm)
*Earias insulana*
*Ectropis* (*Boarmia*) *crepuscularia*
*Ennomos subsignarius* (elm spanworm)
*Ephestia* (*Cadra*) *cautella* (almond moth)
*E. elutella* (tobacco moth)
*E.* (*Anagasta*) *kuehniella* (Mediterranean flour moth)
*Epinotia tsugana* (a skeletonizer)
*Epiphyas postvittana*
*Erannis defoliaria* (mottled umber moth)
*E. tiliaria* (linden looper)
*Erinnysis ello*
*Erigaster henkei*
*E. lanestris*
*Estigmene acrea* (slat marsh caterpillar)
*Eublemma amabilis*
*Euphydryas chalcedona*
*Eupoecilia ambiguella*
*Euproctis chrysorrhoea* (*Nygmi phaeorrhoea*) (brown tail moth)
*E. fraterna*
*E. pseudoconspersa*
*Eupterote fabia*
*Eutromula* (*simaethis*) *pariana*
*Euxoa messoria* (dark-sided cutworm)
*Galleria mellonella* (greater wax moth)
*Gastropacha quercifolia*
*Halisdota argentata*
*H. caryae* (hickory tussock moth)
*Harrisina brillians* (western grapeleaf skeletonizer)
*Heyda nubiferana* (fruit tess totrix moth, green budworm)
*Heliothis* (*Helicoverpa*) *armigera* (Heliothis=-Cloridea) (gram pod borer)
*H.* (*H.*) *assulta*
*Heliothis peltigera*
*H. virescens* (tobacco budworm)
*H. viriplaca*
*H. zea* (cotton bollworm, corn earworm, soybean podworm, tomato fruitworm, sorghum headworm, etc.)
*Hellula undalis* (cabbage webworm)
*Herpetogramma phaeopteralis* (tropical sod webworm)
*Heterocampa guttivitta* (saddled prominent)
*H. manteo* (variable oak leaf caterpillar)
*Holcocera pulverea*
*Homoeosoma electellum* (sunflower moth)
*Homona magnima*
*Hyloicus pinastri*
*Hyphantria cunea* (fall worm)
*Hypogymna morio*
*Itame* (*Thamnonoma*) *wauaria* (a spanworm)
*Junonia coenia* (buckeye caterpillars)
*Kakivoria flavofasciata*
*Keiferia* (*Gnorimoschema*) *lycopersicella* (tomato pinworm)
*Lacanobia* (*Polia*) *olercea*
*Lamdina athasaria pellucidaria*
*L. fiscellaria fiscellaria* (hemlock looper)
*L. fiscellaria lugubrosa* (western hemlock looper)
*L. fiscellaria somniaria* (western oak looper)
*Lampides boeticus* (bean butterfly)
*Leucoma* (*Stilpnotia*) *salicis* (satin moth)
*L. wiltshirei*
*Lobesia* (=*Polychrosis*) *botrana*
*Loxostege commixtalis* (alfalfa webworm)
*L. sticticalis* (beet webworm)
*Lymantria* (*Porthetria*) *dispar* (gypsy moth) (Lymantria: tussock moths)
*L. monacha* (nun-moth caterpillar)
*Malacosoma americana* (eastern tent caterpillar)
*M. disstria* (forest tent caterpillar)
*M. fragilis* (=fragile) (Great Basin tent caterpillar)
*M. neustria* (tent caterpillar, lackey moth)
*M. neustria* var. *testacea*
*M. pluviale* (western tent caterpillar)
*Mamerstra brassicae* (cabbage moth)
*Manduca* (*Inotoparce*) *quinquemaculata* (tomato hornworm)
*M.* (*I.*) *sexta* (tobacco hornworm)
*Maruca testulalis* (bean pod borer)
*Melanolophia imitata*
*Mesographe forficalis*
*Mocis repanda* (Mocis: semilooper)
*Molippa sabina*
*Monema flavescens*
*Mythimna* (*pseudaletia*) *unipuncta* (armyworm)
*Nephantis serinopa*
*Noctura* (*Triphaena*) *pronuba*
*Nomophila noctuella* (lucerne moth)
*Nymphalis antiopa* (morning-cloak butterfly)
*Oiketicus moyanoi*
*Ommatopteryx texana*
*Operophtera brumata* (winter moth)
Opsophanes sp.
*O. fagata*
*Orgyis* (*Hemerocampa*) *antiqua* (rusty tussock moth)
*O. leucostigma* (white-marked tussock moth)
*O.* (*H.*) *pseudotsugata* (Douglas-fir tussock moth)
*O. thyellina*
*Orthosia gothica*
*Ostrinia* (*Pyrausta*) *nubilalis* (European corn borer)
*Palacrita vernata* (spring cankerworm)
*Pammene juliana*
*Pandemis dumetana*
*P. pyrusana*
*Panilis flammea*
*Papilio cresphontes* (orange dog)
*P. demoleus*
*P. philenor*
*Paralipsa* (*Aphemia*) *gularis*
*Paralobesia viteana*
*Paramyelois transitella*
*Parnara guttata*
*Pectinophora gossypiella* (pink bollworm)
*Pericallis ricini*
*Peridrima saucia* (variegated vutworm)
*Phalera bucephala*
*Phlogophora meticulosa*
*Phryganidia californica* (California oakworm)
*Phthorimaea* (=*Gnorimoschema*) *operculella* (potato tuberworm)
*Phylonorycter* (*Lithocolletis*) *blancardella* (spotted tentiform leafminer)
*Pieris brassicae* (large white butterfly)
*P. canidia sordida*
*P. rapae* (imported cabbageworm, small white butterfly)
*Plathypena scabra* (green cloverworm)
Platynota sp.
*P. sultana*
*Playptilia carduidactyla* (artichoke plume moth)
*Plodia interpunctella* (Indian-meal moth)

*Plutella xylostella* as *maculipennis* (diamond-backed moth)
*Prays citri* (citrus flower moth)
*P. oleae* (olive moth)
*Pseudoplusia includens* (soybean looper)
*Pygaera anastomosis*
*Rachiplusia ou*
*Rhyacionia boliana* (European pine shoot moth)
*Sabulodes caberata* (omonvorous looper)
*Samia cynthis* (cynthis moth)
*Saturnia pavonia*
*Schirzura concinna* (red-humped caterpillar)
*Schoenobius bipunctifer*
*Selenephera lunigera*
*Sesamia inferens*
*Sibine apicalis*
*Sitotriga cerealella* (Angoumois grain moth)
*Sparganothis pilleriana*
*Spilonota* (Tmetocera) *ocellana* (eye-spotted bud-moth)
*Spilosoma lubricipeda* (as methastri)
*S. virginica* (yellow woolybear)
Spilosoma sp.
*Spodoptera* (*Prodenia*) *eridania* (southern armyworm)
*S. exigua* (beet armyworm, lucerne caterpillar)
*S. frugiperda* (fall leafworm)
*S. littoralis* (cotton
*S. litura*
*S. mauritia* (lawn armyworm)
*S.* (*P.*) *ornithogalli* (yellow-striped armyworm)
*S.* (*P.*) *praefica* (western yellow-striped armyworm)
*Sylleptederogata*
*S. silicalis*
*Symmerista canicosta*
*Thaumetopoea pityocampa* (pine processionary caterpillar)
*T. processionea*
*T. wauaria* (currant webworm)
*T. wilkinsoni*
*Thymelicus lineola* (European skipper)
*Thyridopteryx ephemeraeformis* (bagworm)
*Tineola bisselliella* (webbing clothes moth)
*Trotrix viridana* (oak tortricid)
*Trichoplusia ni* (cabbage looper)
*Udea profundalis* (false celery leaftier)
*U. rubifalis* (celery leaftier, greenhouse leaftier)
*Vanessa cardui* (painted lady)
*V. io*
*Xanthopastis timais*
*Xestia* (*Amathes, Agrotis*) *c-nigrum* (spotted cutworm)
*Yonomeuta cognatella* (=*Y. evonymi*) (*Yponimeuta*=-*Hyponomeuta*)
*Y. evonymella*
*Y. mahalebella*
*Y. malinella* (small ermine moth)
*Y. padella* (small ermine moth)
*Y. rorrella*
*Zeiraphera diniana*

MALLPHAGA
*Bovicola bovis* (cattle biting louse)
*B. crassipes* (Angora goat biting louse)
*B. limbata*
*B. ovis* (sheep biting louse)
*Lipeurus caponis* (wing louse)
*Menacnathis stramineus* (chicken body louse)
*Menopon gallinae* (shaft louse)

TRICHOPTERA
*Hydropsyche pellucida*
*Potamophylax rotundipennis*

TABLE 2

| | *Bacillus thuringiensis* subspecies | | |
|---|---|---|---|
| Subspecies | Gene Location[1] | Toxicity[2] | Availability[3] |
| *alesti* | P | L | USDA, ATCC |
| *aizawai* | P | L, D | USDA |
| *canadensis* | | | USDA |
| *colmeri* | | | USDA |
| *dakota* | | L | USDA |
| *darmstadiensis* | P | D | USDA |
| *dendrolimus* | C | | USDA, ATCC |
| *entomocidus* | C | L | USDA, ATCC |
| *finitimus* | P, C | L | USDA, ATCC |
| *galleriae* | P | L | USDA, ATCC |
| *indiana* | | L | USDA |
| *israelensis* | P | D | ATCC |
| *kenyae* | | L, D | USDA |
| *kurstaki* K-1 (HD-1) | P | L, D | USDA, ATCC |
| *kurstaki* K-73 (HD73) | P | L | USDA, ATCC |
| *kumanotoensis* | | | USDA |
| *kyushuensis* | C | D | USDA |
| *morrisoni* | P | L | USDA |
| *ostriniae* | | L | USDA |
| *pakistani* | | L | USDA |
| *san diego* | | C | 4 |
| *sotto* | P | | USDA, ATCC |
| *subtoxicus* | P, C | | USDA, ATCC |
| *tenebrionis* | | C | DSM |
| *thompsoni* | P | | USDA |
| *thuringiensis* | P, C | L, D | ATCC |
| *tochigiensis* | | | USDA |
| *tolworthi* | P | L | USDA |
| *tohokuensis* | | | USDA |
| *toumanoffi* | P | | USDA |
| *wuhenensis* | P | | USDA |

[1]Crystal protein gene located on a plasmid (P), on the chromosome (C) or both. See Aronson et al. (1986) Microbiol. Rev. 80:1-24.
[2]L = Lepidopteran; D = Dipteran; C = Coleopteran; not all strains of any one variety may display the same toxicity range; the absence of a notation in this column does not indicate that the strain is nontoxic to insects.
[3]Strains of these varieties are publicly available from depositories: USDA = United States Department of Agriculture, Agricultural Research Service, Cotton Insect Research, P.O. Box 1033, Brownsville, Texas. ATCC = American Type Culture Collection, 12301 Parklawn Drive, Rockville, Maryland. DSM = Deutsche Sammlung von Mikroorganismen, Schnitsphanstrasse Darmstadt, Federal Republic of Germany. Strains of *Bacillus thuringiensis* varieties are also available from Northern Regional Research Laboratory, 1815 North University Street, Peoria, Illinois; and from The Collection of Strains of *Bacillus thuringiensis* and *Bacillus sphaericus*, Laboratoire de Lutte Biologique (II), H. de Barjac, Institut Pasteur, 25 Rue du Docteur Roux, 75724 Paris Cedex 15, France.
[4]*B. thuringiensis* var. *san diego* is described in Herrnstadt et al. (1986) Biotechnology 4:305-309.

A single strain of *Bacillus thuringiensis* may contain more than one distinct crystal protein gene (Kronstad et al. (1983) J. Bacteriol. 154:419-428). In particular, it was demonstrated that *B. thuringiensis* HD-1 Dipel plasmids contain three distinct crystal protein genes. These distinct genes may encode toxic proteins with varying insect specificities (Calabrese et al. (1980) Can. J. Microbiol. 26:1006-1010; and Jarrett (1985) J. Appl. Bacteriol. 58:437-448). For example, the presence of multiple genes encoding different toxic proteins may be responsible for the combined lepidopteran and dipteran toxicity of certain strains of *Bacillus thuringiensis* (Yamamoto and McLoughlin (1981) Biochem. Biophys. Res. Comm. 103:414-421).

Genes encoding crystal proteins have been identified and cloned from several varieties of *Bacillus thuringiensis*, including the protoxin genes from kurastaki strains HD-1 and HD-1-Dipel (Whiteley et al. (1982) in *Molecular Cloning and Gene Regulation in Bacilli*, Ganesan et al. (ed) pp. 131-144; Schnepf and Whiteley (1981) Proc. Natl. Acad. Sci. USA 78:2893-2897 and U.S. Pat. Nos. 4,448,885 and 4,467,036), and HD-73 (Schnepf and Whiteley, 1981; Adang et al. (1985) Gene 36:289-300;

U.S. Pat. Nos. 4,448,885 and 4,467,036, Schnepf and Whiteley), berliner 1715 (Klier et al. (1982) EMBO J. 1:791–799), thuringiensis HD2 (Whiteley et al. (1985) in *Molecular Biology of Microbial Differentiation*, Hoch and Setlow (ed.), American Society of Microbiologists, Washington, D.C., p. 225–229), sotto (Shibano et al. (1985) Gene 34:243–251), aizawa (Klier et al.(1985) in *Molecular Biology of Microbial Differentiation*, Hoch and Setlow (ed.), American Society for Microbiology, Washington, D.C., p. 217–224), subtoxicus (Klier al., 1985), israelensis (Sekar (1985) Gene 33:151–158; Ward et al.(1984) FEBS Lett. 175:377–382; Thorne et al.(1986) J. Bacteriol. 166:801–811) and san diego (Herrnstadt et al.(1986) Biotechnology 4:305–308).

The nucleotide sequence of the following crystal protein structural genes have been reported: several genes from kurastaki HD-1-Dipel (Wong et al.(1983) J. Biol. Chem. 258:1960–1967; Schnepf and Whiteley (1985) J. Biol,. Chem 260:6264–6272; Thorne et al., 1986); kurastaki HD-73 (Adang et al. 1985) supra; israelensis mosquitocidal protein gene (Thorne et al., (1986) supra; dendrolimus crystal protein gene N-terminal (Nagamatsu et al. (1984) Agri. Biol. Chem 48:611–619) and sotto crystal protein toxic fragment (Shibano et al. (1985) supra.

*Bacillus thuringiensis* crystal proteins are useful as insecticides because they are highly specific in their toxicity, being totally nontoxic toward most nontarget organisms. Since the protoxin crystals must be ingested for toxicity, crystals must be located where they will be eaten by target insect larvae. The utility of *Bacillus thuringiensis* insecticidal compositions in limited by the fact that they must be applied repeatedly to plants to afford protection, as *Bacillus thuringiensis* is subject to UV inactivation and washoff by rainfall. A solution to this problem is the use of other bacteria which have an affinity for plants (i.e. colonize, proliferate or persist on plants) as vectors for the delivery of insect toxic protein. This can be accomplished by the introduction of crystal protein genes into and the expression of crystal protein toxin by plant colonizing bacteria.

In several cases, cloned *Bacillus thuringiensis* crystal protein genes have been expressed in heterologous strains, including *E. coli* (Schnepf and Whiteley (1982) supra; Adang et al. (1985) supra; Held et al. (1982) Proc. Natl. Acad. Sci. USA 79:6065–6069; Thorne et al. (1986) supra), *B. subtilis* (Held et al. (1985) supra; Thorne et al. (1986) supra, Rhizobium and Agrobacterium strains (U.S. patent application Ser. No. 756,355 (Adang et al.), filed Jul. 18, 1985) and *Pseudomonas fluorescens* (Watrud et al. (1985) in *Engineered Organism in the Environment; Scientific Issues*, Halvorson et al. (eds.), American Society for Microbiology, Washington, D.C.). Crystal protein genes have been expressed in heterologous bacteria under the control of the homologous CP gene promoters or under the control of heterologous promoters.

U.S. patent application Ser. No. 756,355 (Adang et al.), filed Jul. 18, 1985, describes the introduction of complete and partial *Bacillus thuringiensis* HD73 crystal protein protoxin genes into strains of Agrobacterium and Rhizobium. The complete and partial crystal protein coding sequences were cloned into the broad host range vector pRK290 and introduced into these strains. The crystal protein genes were expressed in these bacteria and cells containing the genes were toxic to Tabbaco Hornworm (THW). Plasmids containing the crystal protein genes were unstable in and inhibited the growth of Agrobacterium and Rhizobium cells. Introduction of partial protoxin genes proved to be less destabilizing and inhibitory while still rendering the cells insect toxic. Rhizobium cells carrying partial protoxin genes formed root nodules that were toxic to THW.

It has been reported that a gene encoding the 134 kd molecular weight crystal protein from *Bacillus thuringiensis* var. *kurastaki* HD-1 has been introduced into root-colonizing *Pseudomonas fluorescens* soil isolates. The crystal protein is reported to be expressed in these genetically altered isolates, producing insect toxic *Pseudomonas fluorescens* (Watrud, et al. 1985 supra).

SUMMARY OF THE INVENTION

It is an object of the present invention to provide a method for protecting plants from insect pests.

It is also an object of the present invention to provide biological control agents and insecticidal compositions containing these agents which are useful in methods for protecting plants from insect pests.

It is a further object of the present invention to provide methods and inoculating compositions for protecting plants from insect pests.

It is yet another object of the present invention to provide genetically altered bacteria which contain and express crystal protein genes of *B. thuringiensis.*

In one embodiment, the present invention provides a method of protecting plants from insect pests which comprises genetic alteration of a plant root and leaf colonizing strain of bacterium of the species *Pseudomonas cepacia* by introducing a gene encoding a crystal protein of a strain of *Bacillus thuringiensis* into the plant colonizing strain and inoculating plants with an insecticidally effective concentration of the resultant genetically altered insect toxic strain of *P. cepacia.*

In another embodiment, the present invention provides an insecticidal plant protective composition containing an insecticidally effective concentration of a genetically altered, insect toxic, plant colonizing bacterium of the species *P. cepacia.*

In yet another embodiment, the present invention provides genetically altered plant-colonizing strains of the species *Pseudomonas cepacia* into which a gene encoding a crystal protein of a strain of *B. thuringiens* has been introduced thereby rendering the plant-colonizing strains toxic to insects of the orders Lepidoptera, Diptera or Coleoptera.

In a preferred embodiment, the present invention provides genetically altered strains of plant colonizing *Pseudomonas cepacia* type Wisconsin into which a gene encoding a crystal protein of a *B. thuringiensis* strain has been introduced. Such genetically altered strains of *P. cepacia* type Wisconsin are particularly useful in methods of biological control of agricultural pests and plant protection because in addition to being insect toxic they are good plant colonizers, broad spectrum fungal antagonists and are non-phytopathogenic.

As an example of the preferred embodiment, the present invention provides genetically altered insect toxic strains of the plant root and leaf colonizing bacterium *P. cepacia* 526.

DETAILED DESCRIPTION OF THE INVENTION

Figure 1:
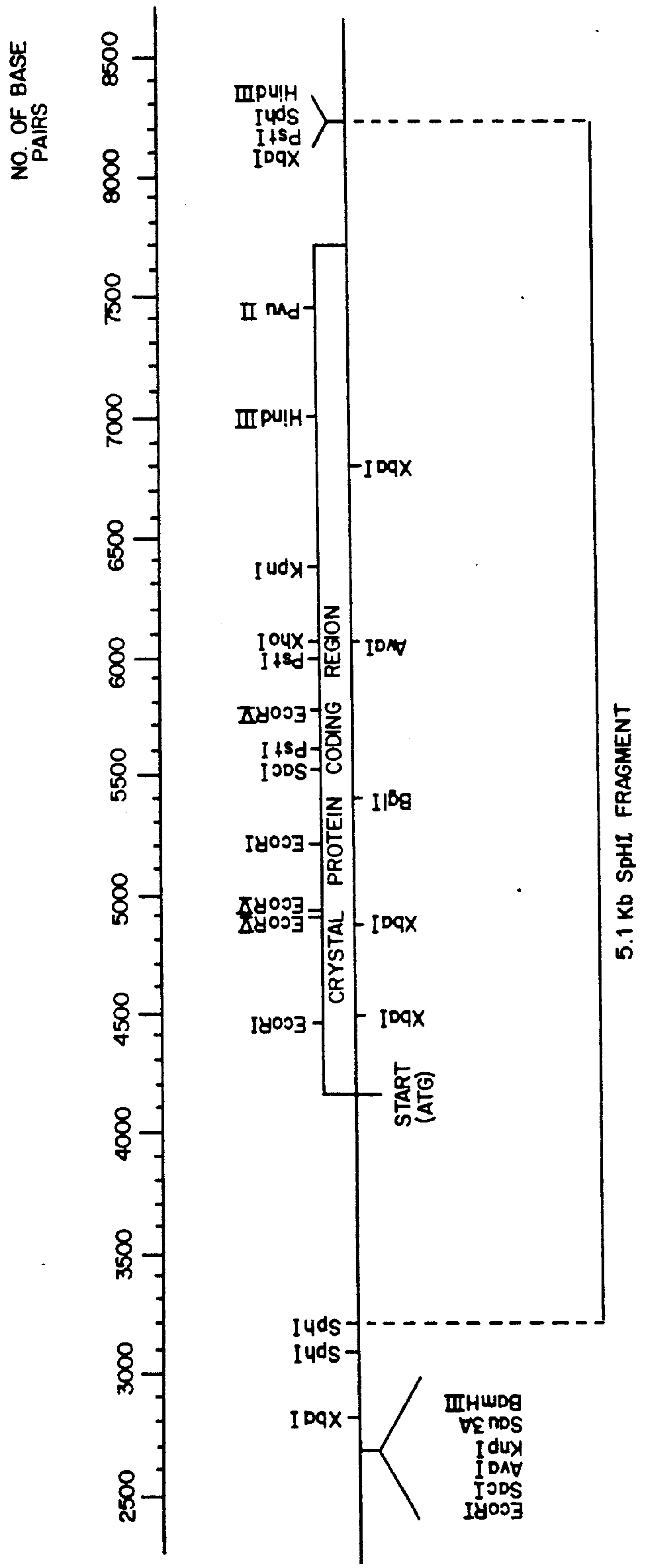
FIG. 1 is a restriction endonuclease map of the relevant portion of DNA fragment 208/43-487. This fragment contains the HD73-like crystal protein gene coding region isolated from *B. thuringiensis* var. *kurstaki* HD-1 Dipel. Restriction sites are indicated using conventional abbreviations. The 5.1 kb SphI fragment is used in the construction of pSUP487 (vide infra). This 5.1 kb SphI fragment contains the full-length coding region of the HD73-like gene and approximately 900 base pairs of 5'-flanking and 500 base pairs of 3'-flanking sequences.

The following definitions are provided for clarity and apply throughout the specification and in the claims.

Crystal protein is used to refer to protein of the parasporal crystals formed in strains of *B. thuringiensis*. Crystal protein is the active agent in insect toxic strains of *B. thuringiensis*. Crystal protein (CP), also often referred to as the $\pi$-endotoxin, may have two forms, a toxin and a precursor, higher molecular weight protoxin. The term crystal protein includes both forms. The toxin is formed from the protoxin by specific cleavage of the carboxy-terminal end of the protoxin. In kurstaki strains the protoxin is a 130 kd protein which is activated (cleaved) in the insect gut to form a 68 kd toxin. A protoxin then is composed of an N-terminal portion in which insect toxicity resides and a dispensable (for toxicity) carboxy-terminal portion. Dipteran and coleopteran insect toxic crystal proteins may also have toxin and protoxin forms.

The term partial protoxin refers to any truncated protoxin molecule lacking a portion of the carboxy-terminus of the protoxin but retaining the portion of the protein essential for toxicity, particularly the carboxy-terminal region of the toxin. A partial protoxin may or may not have a deletion at the amino terminus of the protein. A partial protoxin may also include altered amino acid sequence not in the protoxin, particularly amino acid sequences appended to the carboxy-terminal end of the toxin protein moiety. The primary distinction of a partial protoxin is that it lacks amino acid sequences present in the complete protoxin but that it is toxic to some insects. The term partial protoxin is used particularly in reference to the lepidopteran toxins (HD-1, HD73, etc.) for which it has been demonstrated that such partial protoxins and altered protoxins are toxic to insects on ingestion.

The term crystal protein (CP) gene or CP coding sequence refers to the DNA sequence encoding the insect toxic crystal protein. In cases where the toxin protein is formed from a precursor protoxin, the term describes the sequence encoding the full-length protoxin.

A gene contains a structural portion extending from a 5'- start codon (usually ATG) to a 3'- stop codon (TAG, TGA or TAA), which portion encodes the amino acid sequence of a polypeptide. A gene also contains regulatory sequences, usually external to the structural gene which affect regulation of expression of the structural gene. The promoter is the nucleotide sequence adjacent to the 5'- end of a structural gene which is involved in the initiation of transcription. Promoters contain sequences which insure proper binding and activation of RNA polymerase, influence where transcription will start and affect the level of transcription. Promoter sequences can extend several hundred base pairs 5' to the structural gene.

It may be desirable to construct chimaeric genes in which a structural gene is placed under the regulatory control of a heterologous promoter from another gene. The majority of promoters control initiation of transcription in only one direction, so in order to be placed under the control of a promoter, a structural gene must be located downstream (3'-direction) of the promoter. The distance between the promoter and the structural gene is believed to be important as well. These constraints are understood in the art. The choice of heterologous promoter used in any such chimaeric construction is dependent on level of gene expression and on the kind of selective expression, if any, that is desired. The chosen promoter must be active in the bacterium in which the construction is to be introduced.

The term recombinant DNA molecule is used herein to distinguish DNA molecules in which heterologous DNA sequences have been artificially cleaved from their natural source or ligated together by the techniques of genetic engineering, for example by in vitro use of restriction enzymes or ligation using DNA ligase.

The process of cloning a DNA fragment involves excision and isolation of a DNA fragment from its natural source, insertion of that DNA fragment into a recombinant vector and incorporation of the vector into a microorganism or cell where the vector and its inserted DNA fragment are replicated. The term cloned DNA is used to designate a DNA fragment or molecule produced by the process of cloning and copies (or clones) of the DNA fragment or molecule replicated therefrom.

A microorganism that is isolated from a particular environment is considered to colonize that environment. Thus, bacteria isolated from plant roots are root-colonizing bacteria. The ability of a bacterium to colonize a particular environment can also be assessed as the ability of the bacterium to proliferate or persist in that environment after it is introduced. Thus a bacterium that becomes established and persists on leaf tissue after inoculation, is considered to colonize leaf tissue. The relative ability of bacterial strains to colonize a particular environment can be measured as in Example 5 (Table 6). For comparative purposes in this application, tested isolates that were recoverable from plant root or rhizosphere at a level of greater than or equal to about $10^6$ bacteria/g root or soil were considered to be good root and/or rhizosphere colonizers.

The present invention is based on applicants' discovery that genes encoding insect toxic crystal proteins of *B. thuringiensis* can be introduced into plant colonizing strains of bacteria of the species *Pseudomonas cepacia* and that these genes are successfully expressed, rendering the genetically altered strains of *P. cepacia* toxic to insects. Plant colonizing insect toxic strains of *P. cepacia* are useful as biological control agents for the protection of plants from insect pests.

Members of the species Pseudomonas cepacia are non-fluorescent, non-denitrifying, nutritionally versatile bacteria, which are further distinguishable from other species of Pseudomonas by a number of biochemical and nutritional criteria that are summarized in Palleroni and Holmes (1981) Int. J. System. Bacteriol. 31:479–481 and Palleroni (1983) "Pseudomonadaceae" in Bergey's Manual of Systematic Bacteriology, Vol. 1, Krieg (ed), Williams and Wilkins, Baltimore, Md p. 140–219. Members of the species *P. cepacia* are ubiquitous to soil environments but do not normally predominate in soil since they are outgrown by fluorescent pseudomonads. Strains of *P. cepacia* have also been isolated from rotten onions and clinical samples. At one time the designation *P. cepacia* was limited to phytopathogenic onion isolates. Now, soil isolates, earlier designated *P. multivorans*, and clinical isolates, earlier designated *P. kingii*, are included in the species *P. cepacia*.

U.S. Pat. No. 4,798,723, filed Jul. 28, 1986) reports the identification of root colonizing strains of non-fluorescent, non-denitrifying, nutritionally versatile Pseudomonas strains from unsterile corn root macerates. These corn root isolates have been identified by classical biochemical and nutritional criteria (see Table 4 for examples of assays used) as belonging to the species *P. cepacia*. Some of these isolates, those obtained from corn roots and cornfield soil originating from sites near Prescott, Wis., USA, can be grouped and distinguished from other *P. cepacia* strains. This novel group of *P. cepacia* strains has been designated *P. cepacia* type Wisconsin. Table 3 is a list of several *P. cepacia* strains that have the distinguishing characteristics of *P. cepacia* type Wisconsin. All of the strains in Table 3 were isolated from Wisconsin cornfield samples. U.S. Pat. No. 4,798,723, which is hereby incorporated by reference, provides reproducible methods for isolation of *P. cepacia* type Wisconsin strains. Representative examples of *P. cepacia* type Wisconsin, *P. cepacia* 406 and *P. cepacia* 526 have been placed on deposit with the American Type Culture Collection, 12301 Parklawn Drive, Rockville, Md., with the accession numbers ATCC 53266 and ATCC 53267, respectively. *P. cepacia* type Wisconsin strains are distinguished in that they are good colonizers of plant roots and rhizosphere, as well as colonizers of plant leaves, are broad spectrum fungal antagonists, particularly of fungi of the genus Fusarium, are non-phytopathogenic, and are effective for the protection of plants against fungal infection and invasion. *P. cepacia* type Wisconsin strains are particularly effective for the protection of corn plants from the pathogen *Fusarium moniliforme*. Although initially isolated from corn root, *P. cepacia* type Wisconsin strains were found to colonize the roots of diverse plants including corn, sorghum, rape, sunflower, wheat, alfalfa, cotton, soybean, peas, tomato and French bean. These bacteria were also found to colonize the leaves of several different plants, including tobacco, cotton and Cape Primrose (Streptocarpus).

*P. cepacia* type Wisconsin strains have broad spectrum anti-fungal activity against fungi of the classes Ascomycetes (i.e., Sclerotinia spp.), Phycomycetes (i.e., Pythium spp.), Basidomycetes (i.e., Rhizoctonia spp.) and *Fungi Imperfecti* (i.e., Fusarium spp.).

TABLE 3

| | *Pseudomonas cepacia* type Wisconsin |
|---|---|
| Strain[1] | Source[2] |
| 406 | site a, Jacques corn parental line 1 isolated oiginally on nutrient agar |
| 526 | site a, Jacques corn parental line 86 isolated on King's B medium |
| 462 | site a, Jacques corn parental line 13 isolated on combined carbon medium |
| 531 | site b, hybrid corn line 7780 isolated on King's B medium |
| 504 | site b, hybrid corn line 7780, isolated on combined carbon medium |

[1]All typed to *P. cepacia* using conventional criteria. See Palleroni and Holmes, 1981, and Bergey's Manual of Systematic Bacteriology VI (1984).

[2]Original root material taken from test fields of Jacques Seed Company, Prescott, Wisconsin. Site a is the field of the experimental station which has been in continuous corn cultivation for 40 years. Site b is the demonstration planting field at the seed processing plant in Prescott, Wisconsin. Site a and site b are several kilometers apart.

TABLE 4

Characterization and comparison of *P. cepacia* root isolates and culture collection strains

| REACTIONS/ENZYMES | 526 | 406 | 64 | 65 | ATCC 29424 | ATCC 17460 | ATCC 25416 | ATCC 10856 | ATCC 17616 | 64-22 NS/NK |
|---|---|---|---|---|---|---|---|---|---|---|
| reduction of nitrates to nitrites | + | + | 0 | 0 | + | 0 | 0 | 0 | + | |
| reduction of nitrates to nitrogen | 0 | 0 | 0 | 0 | 0 | + | 0 | 0 | 0 | |
| indole production | 0 | 0 | 0 | 0 | 0 | 0 | 0 | 0 | 0 | |
| acidification with glucose | 0 | 0 | 0 | 0 | 0 | 0 | 0 | 0 | 0 | |
| arginine dihydrolase | 0 | 0 | 0 | 0 | 0 | 0 | 0 | 0 | 0 | |
| urease | 0 | 0 | 0 | 0 | 0 | 0 | 0 | 0 | 0 | |
| hydrolysis (β-glucosidase) | + | + | + | + | 0 | + | + | + | 0 | |
| hydrolysis (protease) | + | + | + | + | 0 | + | + | 0 | 0 | |
| β-galactosidase | + | + | + | + | + | + | + | + | + | |
| glucose assimilation | + | + | + | + | + | + | + | + | + | |
| arabinose assimilation | + | + | + | + | + | + | + | + | + | |
| mannose assimilation | + | + | + | + | + | + | + | + | + | |
| mannitol assimilation | + | + | + | + | + | + | + | + | + | |
| N-acetyl-glucosamine assimilation | + | + | + | + | + | + | + | + | + | |
| maltose assimilation | 0 | 0 | 0 | 0 | 0 | 0 | 0 | 0 | 0 | |
| gluconate assimilation | + | + | + | + | + | + | + | + | + | |
| caprate assimilation | + | + | + | + | + | + | + | + | + | |
| adipate assimilation | + | + | + | + | + | + | + | + | + | |

TABLE 4-continued

Characterization and comparison of *P. cepacia* root isolates and culture collection strains

| REACTIONS/ENZYMES | 526 | 406 | 64 | 65 | ATCC 29424 | ATCC 17460 | ATCC 25416 | ATCC 10856 | ATCC 17616 | 64-22 NS/NK |
|---|---|---|---|---|---|---|---|---|---|---|
| malate assimilation | + | + | + | + | + | + | + | + | + | |
| citrate assimilation | + | + | + | + | + | + | + | + | + | |
| phenyl-acetate assimilation | + | + | + | + | + | + | + | + | + | |
| cytochrome oxidate | 0 | 0 | 0 | 0 | 0 | 0 | 0 | + | + | |
| Motility | + | + | + | + | + | + | + | + | + | |
| Gram staining | − | − | − | − | − | − | − | − | − | |
| Pigmentation | yellow | pale yellow | white | white | | | | | | yellow |
| Plate inhibition (in vitro) of: | | | | | | | | | | |
| *Fusarium moniliforme* | 4 | 4 | 4 | 2 | 3 | 5 | 5 | 0 | 0 | 4 |
| Sclerotinia sp. | 4 | 4 | 5 | 2 | 0 | 4 | 1 | 0 | 0 | ND |
| Macrophomina sp. | 3 | 3 | 2 | 1 | 1 | 2 | 2 | 0 | 0 | ND |
| Plant bioassay - % reduction in seedling infection | 62 | 81 | 24 | 0 | 0 | 0 | 4.36 | 5.96 | 33.7 | 0-2.52 |
| Onion pathogenicity test | 1 | 0 | 3 | 3 | 4 | 1 | 3 | 1 | 0 | 4 |
| Corn root colonization at 2 weeks cfu/g dry wt root log 10 units | 6.60 | ND | ND | ND | 6.86 | 6.01 | 5.60 | 6.06 | 6.72 | 6.73-7.10 |

In principle, any plant colonizing strain of *P. cepacia* can be used in the present invention as a "vector" for delivering to that plant an insect toxic crystal protein. *P. cepacia* type Wisconsin strains are preferred "vectors" because they are not pathogenic to plants and colonize diverse plants. Since these strains are found to colonize and persist on both plant roots and leaves, they are useful for carrying insect toxic proteins to both of these plant environments to protect a plant from root and foliar insect damage.

The activity spectrum of crystal toxins varies among varieties and strains of *B. thuringiensis* and is correlated with the presence of distinct crystal proteins and genes encoding them. Different crystal proteins are responsible for the toxicity displayed by *B. thuringiensis* varieties against insects belonging to different families. For example, kurstaki strains contain CP specific for Lepidopterans, israelensis strains contain CP specific for Dipterans and tenebrionis and san diego strains contain CP specific for Coleopterans. The activity of some kurstaki strains against Lepidopterans and Dipterans is due to the presence of at least two different crystal proteins. Activity range toward insects within a particular family is also correlated with the presence of multiple CP and genes encoding them. It is not yet known what structural features of the CP genes are associated with the varying insect specificities of the toxins.

The methods of the present invention can utilize any of the crystal protein genes of *B. thuringiensis* . Partial protoxin genes can also be employed i& desired. The specific crystal protein genes or coding sequences introduced into root colonizing *P. cepacia* are chosen to obtain the desired toxicity range for the resultant genetically altered bacterium. If it is desirable, more than one CP gene can be introduced into a single strain of *P. cepacia*. It is also contemplated that any *P. cepacia* active promoter sequences can be used in the construction of CP chimaeric genes.

It has been demonstrated, at least with the Lepidopteran specific crystal proteins, like HD73 CP, that the full-length crystal protein coding region need not be expressed by a cell to produce insect toxic proteins. U.S. patent application Ser. No. 617,321, (M. J. Adang), filed Jun. 4, 1984, teaches the use of DNA plasmids carrying partial crystal protein genes to produce insect toxic proteins and bacterial cells. Expression of partial crystal protein genes (i.e., partial protoxin genes) produces partial protoxins, which are precursors of toxins.

In an exemplary embodiment of the present invention, genes encoding crystal protein insect toxins were introduced into a strain of *P. cepacia* type Wisconsin. Specifically the genes encoding the HD73 and HD73-like genes derived from *B. thuringiensis* var. *kurstaki* strains HD73 and HD-1 Dipel, respectively, were introduced into *P. cepacia* 526 by cloning the crystal protein encoding sequences into incompatibility group Q (IncQ) plasmids and introducing these plasmids into the *P. cepacia* type Wisconsin 526 strain.

Figure 3:
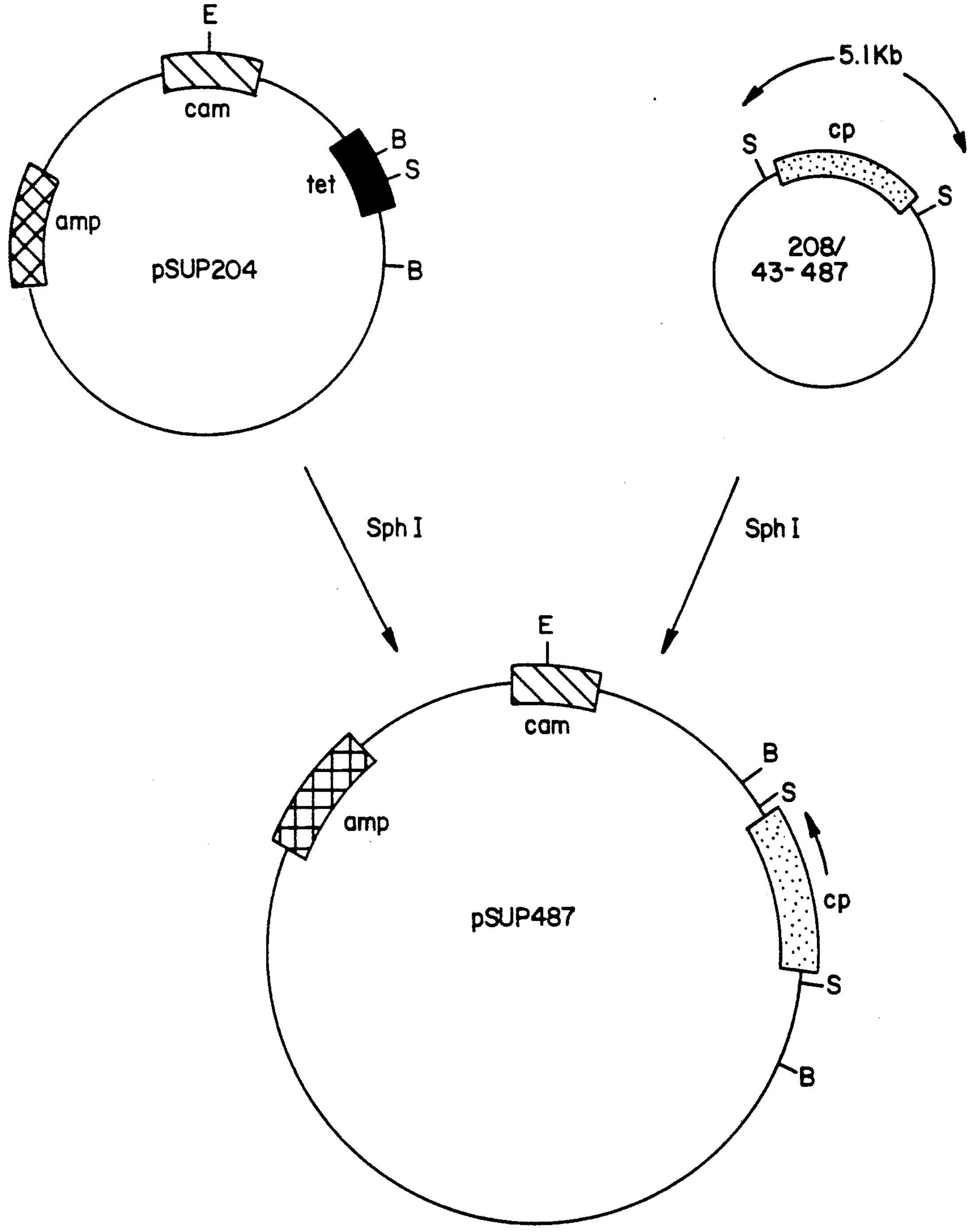
FIG. 3 is a diagram of the construction of plasmid pSUP487. The SphI fragment containing HD73-like crystal protein sequences is indicated. Restriction sites are indicated as follows: S=SphI; B=BamHI; E=EcoRI. Antibiotic markers carried by the various constructions are indicated. The direction of transcription of the crystal protein gene in the construct pSUP487 is indicated by an arrow.

In one genetic construction of the present invention, designated pSUP487, the CP HD73-like gene derived from the HD-1 Dipel *B. thuringiensis* strain remained under the regulatory control of its homologous *B. thuringiensis* promoter sequences. In another construction, designated pSKP/Bt the HD73 structural gene from *B. thuringiensis* HD73 was placed under the regulatory control of a heterologous promoter, the nptII gene promoter from the transposon Tn5, which was known to be active in *P. cepacia* strains. Both of these plasmids are reproducibly prepared from readily available starting materials, as described in examples 1 and 2 and diagrammed in FIGS. 3 and 4.

The recombinant plasmids containing the CP sequences were introduced into *P. cepacia* 526 using conventional triparental mating techniques. Both *P. cepacia* transconjugants, *P. cepacia* 526(pSUP487) and *P. cepacia* 526(pSKP/Bt), expressed several proteins that reacted with crystal protein antibody. The proteins detected on western blots ranged in size from about 70 to 92 kd, but no protein bands corresponding in size to the HD73 protoxin (130 kd) or the toxin (68 kd) were detected. The proteins expressed using either construction were similar, but the level of expression appeared to be higher from the nptII promoter. The proteins detected are believed to represent the products of incomplete transcription of the complete CP structural gene, but such aberrant size products could also result from CP gene sequence deletions.

Genetically altered *P. cepacia* 526 transconjugants containing *B. thuringiensis* CP sequences were found to be insect toxic using diet assays (Table 5) and assays on excised leaf (Table 7) and whole plants (Table 8). Cell suspensions of *P. cepacia* 526 containing either pSUP487 or pSKP/BT applied to the surface (about $4\times10^5$ bacteria/$cm^2$) of an artificial diet were found to be toxic to Tobacco hornworm (THW, Manduca sexta) neonate larvae (Table 5). In this experiment, a ten-fold dilution of the bacterial suspension decreased larvae mortality.

Excised tobacco leaves were protected from THW damage by inoculation with *P. cepacia* 526(pSUP487) or 526(pSKP/Bt). Tobacco leaves were sprayed with seruspensions of both *P. cepacia* 526 transconjugants (about $1\times10^8$ bacteria/ml) and neonate THW larvae were placed on leaves. Significant larval killing was noted on treated leaves which showed no sign of insect damage. Uninoculated and control leaves were devoured.

Young tobacco plants were sprayed with bacterial suspensions of *P. cepacia* transconjugants, *P. cepacia* 526(pSUP487) and 526(pSKP/BT) (about $5\times10^{10}$ bacteria/ plant). After bacterial inoculation, THW larvae were placed on plant leaves. As shown in Table 9, larval mortality on plants inoculated with *P. cepacia* 526 (pSUP487) and 526 (pSKP/Bt). Inoculation with genetically altered insect toxic *P. cepacia* protected plants from insect damage.

In an exemplary embodiment of the present invention, *P. cepacia* strains were genetically altered by introduction of a recombinant vector which carried the desired crystal protein gene construction. While this method rendered the transformed bacteria insect toxic and capable of protecting plants on which they were inoculated from insect pests, it was found that the introduced recombinant vectors were not stably maintained in the bacteria without application of selective pressure. Thus, after a number of generations, the insect toxic phenotype was lost. It may be desirable to increase the stability of insect toxic phenotype in cells. As is well known to those skilled in the art, stabilization can be achieved in several ways including vector stabilization or preferably by integration of the CP gene constructions into the bacterial chromosome. A DNA vector can be stabilized in a bacterial cell by incorporating into the DNA vector a gene that is required for cell survival. This can be done, for example, by preparing an auxotrophic mutant of the bacterium. This mutant must not be capable of survival without complementation of the auxotrophy. A gene or genes that complement the lethal auxotrophic mutation are then placed on the DNA vector along with the CP sequences. Retention of the vector is then required for survival of the cell and the CP sequences are stabilized.

It may not be desirable for environmental reasons to introduce recombinant genes on vectors that may be transmitted in the natural population. For this reason it may be preferred to integrate the CP gene constructions into the bacterial chromosome. Example 8 provides one method of integrating CP sequences into the chromosome using homologous recombination. Other methods and modifications of these methods are well known in the art. For example Barry (1986) Biotechnology 4:446–449 describes a method for stable chromosomal integration of foreign genes which employs a defective transposon.

A primary use of the genetically altered *P. cepacia* of the present invention is the inoculation of plants or their roots to provide protection from insect pests. Root and/or rhizosphere colonization by these *P. cepacia* strains can be accomplished by direct or indirect inoculation of seeds at the time of planting. Direct seed inoculation involves application of an inoculant to the seed prior to sowing. Many variations of preparing such seed inoculants are known in the art. Indirect seed inoculation involves application of an inoculating material into the vicinity of the seed at the time of planting.

In order to establish leaf colonizing strains on plant leaves, it is only necessary to inoculate leaves with an appropriate composition containing the desired strain. Foliar inoculants can be applied, in principle, at any time during growth of the plant. Inoculation by spraying of liquid or particulate inoculating compositions is particularly useful.

The concentration of insect toxic bacteria that will be required to produce insecticidally effective inoculating compositions will depend on the strain of *P. cepacia* utilized, the exact CP gene construction used, and the formulation of the composition. The concentration of cells required for effective insecticidal activity can be determined by protection assays, for example those described in Examples 6 and 7.

Inoculating compositions must be suitable for agricultural use and dispersal in fields. Generally, components of the composition must be non-phytotoxic, non-bacteriostatic and non-bacteriocidal. Foliar applications must not damage or injure plant leaves. In addition to appropriate liquid or solid carriers, inoculating compositions may include sticking and adhesive agents, emulsifying and wetting agents, and bacterial nutrients or other agents to enhance growth or stabilize bacterial cells. Inoculating compositions for insect pest control may also include agents which stimulate insect feeding.

Reviews describing methods of application of biological insect control agents and agricultural inoculation are available. See, for example, Couch and Ignoffo (1981) in *Microbial Control of Pests and Plant Disease* 1970–1980, Burges (ed.), chapter 34, pp. 621–634; Corke and Rishbeth, ibid, chapter 39, pp. 717–732; Brockwell (1980) in *Methods for Evaluating Nitrogen-Fixation*, Bergersen (ed.) pp. 417–488; Burton (1982) in *Biological Nitrogen Fixation Technology for Tropical Agriculture*, Graham and Harris (eds.) pp. 105–114; and Roughley (1982) ibid, pp. 115–127.

Except as noted hereafter, standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in: Maniatis et al. (1982) Molecular Cloning, Cold Spring Harbor Laboratory, Cold Spring Harbor, New York; Wu (ed.) (1979) Meth. Enzymol. 68; Wu et al. (eds.) (1983) Meth. Enzymol. 100 and 101: Grossman and Moldave (eds.) Meth. Enzymol. 65; Miller (ed.) (1972) *Experiments in Molecular Genetics*, Cold Spring Harbor Laboratory, Cold Spring Harbor, N.Y.; Old and Primrose (1981) *Principles of Gene Manipulation*, University of California Press, Berkeley; Schleif and Wensink (1982) *Practical Methods in Molecular Biology*; Glover (ed.) (1985) *DNA Cloning* Vol. I and II, IRL Press, Oxford, UK; Hames and Higgins (eds.) (1985) *Nucleic Acid Hybridization*, IRL Press, Oxford, UK; Sellow and Hollaender (1979) *Genetic Engineering: Principles and Methods*, Vols. 1–4, Plenum Press, New York, which are expressly incorporated by reference herein. Abbreviations and nomenclature, where employed, are deemed standard in the field and commonly used in professional journals such as those cited herein.

EXAMPLE 1.1

Isolation of an HD73 CP insect toxin gene from *B. thuringiensis* var. *Kurstaki* HD-1 Dipel DNA hybridization experiments (Kronstad, 1983) showed that *B. thuringiensis* var. *kurstaki* HD-1 Dipel (NRRL deposit, NRRL B-3792) harbors three homologous but distinct crystal protein genes, which are found to be carried on 6.6, 5.3 and 4.5 kb HindIII DNA fragments, respectively. The gene carried on the 4.5 kb fragment, also called the HD-1 crystal protein gene, has been cloned by Schnepf and Whiteley (1981) supra. The gene carried on the 6.6 kb fragment is similar to the crystal protein gene of *B. thuringiensis* var. *kurstaki* HD73 (Adang et al. (1985) supra, and is designated the HD73-like gene herein. The third crystal protein gene (5.3 type) appears to be unique.

The isolation and cloning of the HD73-like CP gene from *B. thuringiensis* var. *kurstaki* HD-1 Dipel is described in Adang et al. (1986) submitted to Biotechnology Advances in Invertebrate Pathology and Cell Culture, Academic Press, N.Y. (issued in 1987 at pages 85-99) Briefly, *B. thuringiensis* plasmid DNA, 30 MD and larger, was prepared by the procedure of Kronstad et al. (1983) supra. A Sau3A partial digest of the plasmid DNA was ligated into the vector pUC18 (Norrander, J. (1983) Gene 26:101-106) and transformed into *E. coli* MC1061 (Casadaban and Cohen (1980) J. Mol. Biol. 138:179-207). Transformant colonies were screen by hybridization of the 3.7 kb BamHI fragment of pUC5'BT which contains the HD73 CP gene sequences. Hybridizing colonies were further screened for crystal protein expression by colony immunoblot method using MAb-1, a monoclonal antibody raised to HD73 CP (Adang et al. (1985) supra, and rabbit polyclonal antibody raised to solubilized HD-73 crystals. Bacterial colonies on nitrocellulose filters were lysed in $CHCl_3$ vapor followed by DNAase and lysozyme treatment (Helfman et al. (1983) Proc. Natl. Acad. Sci. USA 80:31-35). Filters were treated with rabbit polyclonal antiserum or MAb-1, followed by detection using an alkaline phosphatase ELISA system (Blake et al. (1984) Anal. Biochem. 136:175-179).

Several colonies were selected by immunological screening; one of these, designated *E. coli* (pBTI-89A) was chosen for further study. The plasmid pBT1-89A, herein designated 208/43-487 (FIG. 1) contained the HD73-like (6.6 kb type) CP gene from *B. thuringiensis* var. *kurstaki* HD-1 Dipel. This recombinant was mapped using restriction enzyme analysis. The restriction enzyme digests of the HD73-like gene are similar if not identical to comparable digests of the HD73 gene. The open reading frame of the HD73-like gene containing the same EcoRI, XbaI, EcoRV, BglII, SacI, PstI, AvaI, XhoI, KpnI, HindIII and PvuII sites contained in the HD73 gene.

EXAMPLE 1.2

Isolation of crystal protein insect toxin genes from *Bacillus thuringiensis* var. *kurstaki* HD73

Figure 2:
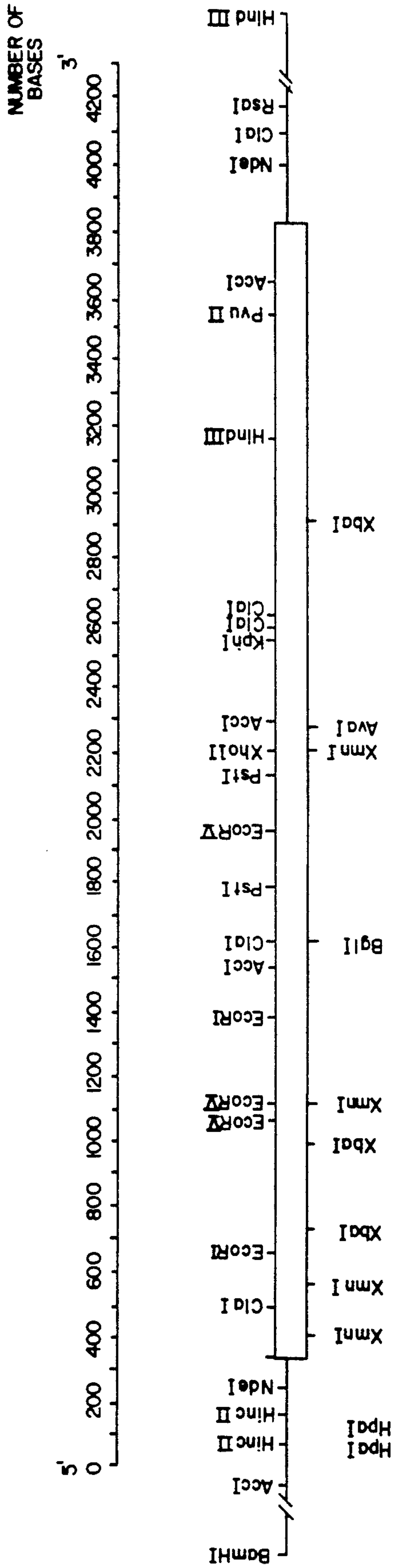
FIG. 2 is a restriction endonuclease map of the relevant portion of DNA fragment 158/51-16. This 10.58 kb fragment contains the HD73 crystal protein gene coding region isolated from *B. thuringiensis* var. *kurstaki* HD73. Restriction sites are indicated using conventional abbreviations. This DNA fragment is the source of crystal protein structural gene sequences used in the construction of pUC5'Bt and subsequently pSKP/Bt.

The crystal protein (CP) gene in *B. thuringiensis* var. *kurstaki* HD73 (NRRL B-4488) is located on a 75 kb plasmid. The molecular cloning of full-length and partial protoxin genes of HD73 CP has been described previously (Adang et al. (1985) Gene 36:289-300; and in U.S. patent application Ser. Nos. 535,354 (Kemp/Adang), filed Sep. 24, 1983; 848,733 (Kemp/Adang), filed Apr. 4,1986; and 617,321 (Adang), filed Jun. 4, 1984). A plasmid, pBt73-16, containing the full-length coding region of the HD73 CP gene was described and has been placed on deposit with The Northern Regional Research Laboratory in strain *E. coli* HB101 (pBt73-16) with accession no. NRRL B-15759. The plasmid pBt73-16 is designated clone 158/51-16, herein (FIG. 2). This clone (158/51-16) contains the full-length HD73 CP coding region.

The plasmid pUC5'Bt contains the HD73 CP sequences from clone 158/51-16 in which a BamHI restriction site was created by oligo-directed site specific mutagenesis 7 base pairs 5' to the ATG start codon of the CP structural gene. This construction allows the removal of the 5'-promoter sequences of the CP gene to produce a "promoterless" CP gene. The plasmid pUC5'Bt was constructed from 158/51-16 as follows:

The 3.7 kb NdeI fragment from 158/51-16 (FIG. 2) was blunt-ended with DNA polymerase (Klenow fragment) and cloned into the SmaI site of M13mp19 (Norrander et al., 1983). After several plaque purifications, one clone was identified and designated 1.6.4. The crystal protein sequences in this clone were oriented so that the BamHI site of the M13 polylinker was at the 3' end of the CP sequences. This is important for the subsequent use of the mutagenized clone in the construction of pUC5'BT and pSKP/Bt.

Next, single stranded DNA from 1.6.4 was used as a template for oligo-directed site-specific mutagenesis using methods described in Norrander et al. (1983) Gene 26:101-106. The oligonucleotide used for mutagenesis was a 25-mer having the following sequence: 5'-GAGATGGAG'GATCCTTATGGATAAC-3'. This oligonucleotide spans the CP gene sequence from bases −16 to +9 (to the ATG start codon). The restriction enzyme cutting site is indicated by "'". Nucleotides 11-13 of the oligonucleotide are mismatched to the CP gene sequence and provide the BamHI restriction (5'-G'GATCC-3') site. Mutagenized clones were selected by probing plaque lifts with radioactively-labeled 25-oligomer. Blots were washed at first at room temperature and autoradiographed. Blots were then rewashed at 48° C. and autoradiographed. Mutagenized clones containing the sequence of the 25-mer give a darker hybridization signal than clones containing wild-type sequence after the 48° C. wash (Norrander et al. 1983) supra. Presumptive mutant clone selections were further characterized by restriction analysis using BamHI endonuclease, which generates an approximately 3.7 kb BamHI fragment not found in the wild-type DNA. This fragment contains the "promoterless" CP sequences. The 5'- BamHI site is from the mutagenesis and the 3'-BamHI site is derived from M13 sequences. This 3.7 kb BamHI fragment was inserted into the vector pUC19 to give plasmid pUC5'BT.

EXAMPLE 2

Introduction of B.t. insecticidal toxin genes into Pseudomonas cepacia 526

Two plasmids were constructed to facilitate introduction of the insect toxic crystal protein into *P. cepacia* 526. Both of these constructions are derivatives of incompatibility group Q (IncQ) plasmids which were found to conjugate into *P. cepacia* 526 at high frequencies and also to be stably maintained. Incompatibility group P plasmids like pRK290 would not conjugate into *P. cepacia* 526.

The first construction, designated pSUP487, is a derivative of the IncQ plasmid pSUP204 (Priefer et al. (1985) J. Bacteriol. 163:324–330) into which the promoter and coding regions of the HD73 CP gene from *B. thuringiensis* var. *kurstaki* HD-1 Dipel was cloned. A 5.1 kb SphI fragment of clone 208/43-487 (FIG. 2) containing the CP gene coding region and approximately 0.9 kb of 5′ and 0.5 kb of 3′ sequences flanking the coding region was cloned into the single SphI site of pSUP204, as diagrammed in FIG. 3. The resultant plasmid DNA was isolated and introduced into *E. coli* HB101, after which chloramphenicol-resistant, tetracycline-sensitive transformants were selected. Plasmid DNA from these selections was isolated and subjected to restriction enzyme analysis to confirm the presence of the CP containing fragment. One of the selections that was shown to contain the CP fragment was chosen and the isolated plasmid was designated pSUP487.

The second construction, designated pSKP/Bt, is a derivative of the IncQ plasmid pSUP104 (Priefer et al., 1985) supra), which carries a "promoterless" CP gene derived from *B. thuringiensis* var. *kurstaki* HD73 under the regulation of the nptII gene promoter sequences derived from the transposon Tn5.

The plasmid pKS4 was the source of the nptII promoter sequences. This plasmid is a derivative of pBR322 which contains the nptII kanamycin resistance gene from transposon Tn5. This plasmid can be obtained from *E. coli* C600 (pKS4) which is on deposit with NRRL with accession no. NRRL B-15394. The plasmid pKS4.6 was constructed from pKS4 as described in U.S. patent application Ser. No. 788,984 filed Oct. 19, 1985, which is hereby incorporated by reference. The feature of pKS4.6 that is important for the construction of pSKP/Bt is that it has been engineered to contain a BamHI restriction site 6 base pairs 5′ to the ATG start codon of the nptII structural gene. This restriction site was created by use of oligo-directed site specific mutagenesis (Norrander, 1983) supra). The presence of this restriction site allows the nptII gene promoter to be removed on an approximately 350 bp HindIII-BamHI fragment of pKS4.6. As diagrammed in FIG. 4, a small HindIII-BamHI fragment was removed from pSUP104 and replaced with the nptII promoter fragment to produce plasmid pSKP. Transformants containing pSKP are chloramphenicol-resistant and tetracycline-sensitive. The pSKP construction is distinguishable by the presence of a BglII restriction site, not present in pSUP104.

Figure 4:
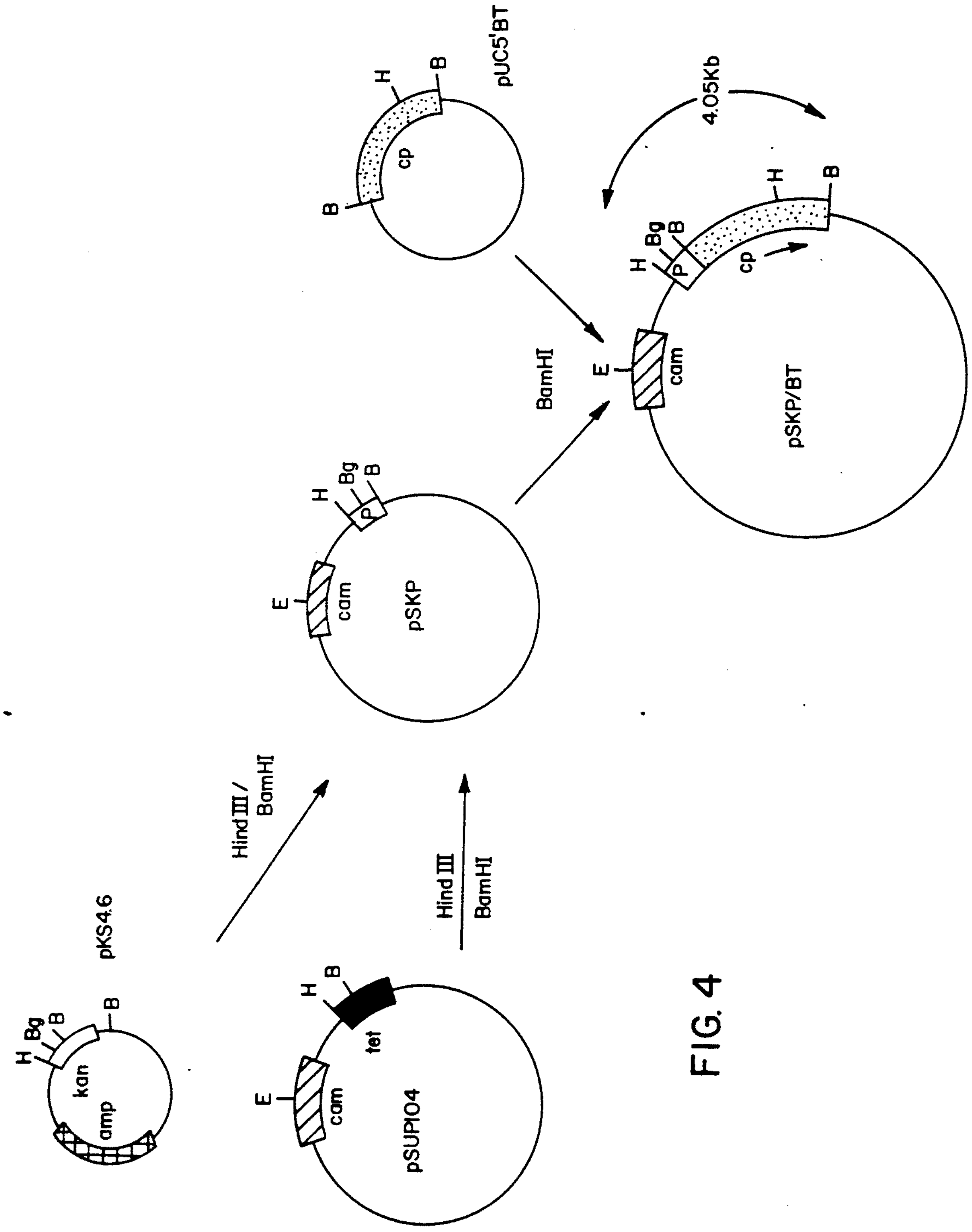
FIG. 4 is a diagram of the construction of plasmid pSKP/Bt. Restriction sites are indicated as follows: B=BamHI; E=EcoRI; H=HindIII; Bg=BglII. Antibiotic markers carried by the various constructs are indicated. The HindIII-BamHI fragment that carries the nptII gene promoter region from Tn5 is indicated in the pSKP and pSKP/Bt by the letter P. The approximately 4.05 kb fragment of pSKP/Bt which carries the nptII promoter/crystal protein structural gene chimaera is indicated. The direction of transcription of the crystal protein sequences in pSKP/Bt is indicated by an arrow.

Promoterless HD73 CP gene sequences were derived from plasmid pUC5′Bt, the construction of which is described above. This plasmid contains a BamHI restriction site 7 base pairs 5′ to the CP gene start codon. The promoterless CP gene can then be removed from pUC5′Bt as an approximately 3.7 kb BamHI fragment (FIG. 4).

The 3.7 kb BanHI fragment from pUC5′BT was cloned into the single BamHI site of pSKP. The resultant ligation mixture was transformed into *E. coli* HB101 and chloramphenicol-resistant transformants were selected. Plasmid DNA from these selections was examined by miniprep techniques (Maniatis et al. (1982) supra), and the orientation of insertion of the CP sequences with respect to the nptII promoter was determined by restriction enzyme analysis using HindIII digests. One of the selected transformants which contained a plasmid in which the CP sequences were inserted in the desired orientation was chosen and designated pSKP/Bt. In this construction (FIG. 4), the 5′ end of the CP structural gene is adjacent to the 3′ end of the nptII promoter sequences so that the CP gene is under the regulatory control of the nptII promoter. The composite or chimaeric nptII promoter/CP structural gene can be removed from the pSKP/Bt plasmid on an approximately 4.05 kb HindIII-BamHI fragment.

Recombinant plasmids pSUP487 or pSKP/Bt were introduced into *P. cepacia* 526 using conventional methods of triparental matings employing the plasmid pRK2013 (Ditta et al. (1980) Proc. Natl. Acad. Sci. USA 77.7347–7357)as a mobilizer. The presence of pSUP487 or pSKP/Bt in *P. cepacia* 526 transconjugants was confirmed by restriction enzyme analysis and Southern blot analysis using the 3.7kb BamHI fragment of pUC5′BT as a hybridization probe. The *P. cepacia* 526 strains which carry the plasmids pSUP487 and pSKP/Bt are designated conventionally as *P. cepacia* 526(pSUP487) and *P. cepacia* 526(pSKP/Bt).

EXAMPLE 3

Expression of Bt crystal protein by *P. cepacia* 526-Immunodetection of crystal protein Standard western blot analyses (see, for example, Adang et al. (1985) supra), were performed to examine expression of Bt crystal protein in *P. cepacia* 526 (pSUP487) and *P. cepacia* 526(pSKP/Bt).

Total protein obtained from mid-logarithmic phase cultures grown in nutrient broth was separated by SDS-electrophoresis, transferred to nitrocellulose and was first reacted with a rabbit polyclonal antibody raised to Bt crystal protein and then with $^{125}$I-protein A. Polyclonal antibodies to Bt crystal protein were prepared essentially as described in U.S. patent application Ser. No. 617,321 (Adang), filed Jun. 4, 1984. Briefly, crystals were isolated from both *B. thuringiensis* var. *kurstaki* strains HD-1 Dipel and HD73, the crystals were solubilized and the crystal proteins were separated by gel electrophoresis. The 130 kd CP protoxin protein band was excised from the gel, lyophilized and ground to a powder. Rabbits were injected subcutaneously with 50 ng crystal protein powder suspended in complete Freunds' adjuvant followed by two injections (50 ng crystal protein each injection) in incomplete adjuvant over a four week period. For use in western blots, rabbit antibody was cleared by reaction to *E. coli* HB101 total protein and *P. cepacia* 526 total protein.

Protein from the parent *P. cepacia* 526, the two *P. cepacia* 526 transformants, as well as *E. coli* HB101 strains transformed with pSUP487 and pSKP/Bt, were examined. Several proteins bands not found in *P. cepacia* 526 which reacted with CP antibody were identified in both transformed *P. cepacia* 526 strains. None of the protein bands of the *P. cepacia* transconjugants corresponded in size to the protoxin (130 kd) or toxin (68 kd) bands found in *B. thuringiensis* HD73. In contrast, *E. coli* HB101 (pSUP487) produces two protein bands of about 130 and 68 kd which react with CP antibody. *E. coli* HB101 (pSKP/Bt) also produces CP antibody reactive proteins of about 130 and 68 kd, but in addition, this strain produces at least 3 other CP antibody reactive proteins having molecular weights intermediate between 68–130 kd. The CP antibody reactive proteins found in the *P. cepacia* 526 transformants appear to correspond to some of the intermediate size proteins observed in *E. coli* HB101 (pSKP/Bt). There are several potential explanations for the presence of aberrant sized CP proteins in the *P. cepacia* 526 transconjugants. For example, transcription of the CP gene may be prematurely terminated, the full-length protoxin may be degraded or a portion of the plasmid construction may have been deleted.

EXAMPLE 4

Expression of crystal protein in *P. cepacia* 526: Insect bioassays

The insecticidal activity of the *Pseudomonas cepacia* 526 pSUP487 and pSKP/Bt transconjugants against Tobacco Hornworm (Manduca sexta) was determined on standard diet assays (for example, Schesser et al. (1977) Appl. Environ. Microbiol. 33:878-880). The results of one such assay are presented in Table 5. Insects were obtained from commercial sources. Test bacteria were grown overnight in Luria broth with appropriate antibiotics. Culture samples (10 ml) were centrifuged (5,000 rpm, 10 min), washed once with phosphate buffered saline (PBS) to remove residual antibiotics and resuspended in 10 ml of PBS. The number of bacterial colony forming units (cfu/ml) in these cultures ranged from 1.6-4.6×$10^8$ cfu/ml (Table 5). For insect bioassays, 10 μl of each bacterial culture (undiluted) was uniformly applied to the surface (1.3 $cm^2$ surface area) of gelled artificial diet (cummercial Gypsy Moth diet) (1 ml in a 4 ml vial) and the treated diet samples were allowed to dry. In some trials, 10× or 100× dilutions of the cultures were used to treat the diet samples. One THW larva was placed in each vial (10 vials/assay) and all vials were allowed to incubate at 26° C. for 4 days. Neonate larvae are used in bioassays. As shown in Table 5, *P. cepacia* 526 containing either pSUP487 or pSKP/Bt is toxic to THW larvae. No toxicity was displayed by the parent *P. cepacia* 526, *P. cepacia* 526(pSUP204) or PBS medium controls.

TABLE 5

Insect Diet Bioassays

| *P. capacia* Strain | CFU/ml[a] | THW Larvae Mortality (no. alive/total)[b] | | |
|---|---|---|---|---|
| | | Undiluted | Dilutions 10× | 100× |
| 526 | 1.6 × $10^8$ | 10/10 | ND | ND |
| 526(pSUP204) | 4.4 × $10^8$ | 10/10 | ND | ND |
| 526(pSUP487) | 3.1 × $10^8$ | 4/10[c] | 10/10 | 9/9[d] |
| 526(pSKP/Bt) | 4.6 × $10^8$ | 0/10 | 8/10 | 8/8[d] |
| PBS | 4.6 × $10^8$ | 10/10 | ND | ND |

[a]Bacterial counts in undiluted sample; CFU = colony forming units.
[b]ND = not done
[c]Those larvae alive were of reduced size compared to controls.
[d]Larvae either missing or killed by cap.

EXAMPLE 5

Colonization Assay

*Pseudomonas cepacia* 526 has been shown to be a good plant colonizer A spontaneous rifampicin (rif) -resistant mutant of *P. cepacia* 526 was isolated and used in colonization assays. This antibiotic resistance marker is carried on the bacterial chromosome so that rif resistance can be used as a strain marker. Experiments to determine the effect of the presence of CP sequences on the ability of *P. cepacia* 526 to colonize plants were performed using a rif-resistant *P. cepacia* 526(pSUP487) transconjugant. Plasmid stability was also determined in this experiment by measuring the retention of the plasmid-borne chloramphenicol-resistance marker.

Colonization assays were performed on corn plants in greenhouse experiments. Experiments were designed to prevent release of *P. cepacia* 526 transconjugants into the environment. Nested Magenta boxes were used for growing plants. A top box contained a soil planting mix which consisted of 2 parts soil, 2 parts peat, 2 parts perlite, 1 part Turface (Trademark, International Minerals and Chemical Corp., Mundelein, Ill.) and 1 part rice hulls. A bottom Magenta box was used as a water reservoir, which could be replenished when necessary. A wick connected the top and bottom boxes allowing transfer of moisture to the closed top box. Corn seeds were inoculated with 1 ml of a stationary phase culture (approx. 4×$10^9$ cells/seed) of the test strain. Inoculated seeds were then planted in the top Magenta box (1 seed/box, 14 replicas/treatment), covered with soil and then covered with paraffinized sand to avoid contamination. Uninoculated controls were also included.

Four plants from each treatment were harvested at 7, 13 and 20 days after planting. Roots of the harvested plants were washed thoroughly under running tap water and then macerated (15 sec) in a blender in 100 ml of PBS. Rootwash was collected into a stoppered sink containing a few gallons of bleach to insure containment of recombinant strains. Viable cell counts were determined by plating $10^3$, $10^4$ and $10^5$ dilutions of the root macerate solution on nutrient agar plates with no antibiotics added, with 100 μg/ml rifampicin added and with 100 μg/ml rifampicin plus 50μg/ml chloramphenicol (cam). The results of one such colonization assay on corn roots is shown in Table 6. Percent colonization was measured as the percent viable counts of rif-resistant bacteria to total bacteria. Plasmid stability, determined as the percent retention of plasmid drug marker, was measured as the percent viable counts of rif/cam resistant bacteria to rif resistant bacteria. Cycloheximide (150 μg/ml) was added to all plates to inhibit fungal growth.

TABLE 6

Colonization of Corn Roots by *Pseudomonas cepacia* 526 and Transconivgants

| Treatment | CFU/g Roots[a] (Fresh Wt.) (time after planting) 7 Days | 13 Days | 20 Days | % Colonization (time after planting) 7 Days | 13 Days | 20 Days | % Plasmid Retention (time after planting) 7 Days | 13 Days | 20 Days |
|---|---|---|---|---|---|---|---|---|---|
| 526 Rif | 6 × $10^6$ | 1 × $10^6$ | 8 × $10^5$ | 60 | 45 | 42 | — | — | — |
| 526 (pSUP204) | 5 × $10^6$ | 5 × $10^6$ | 1 × $10^6$ | 90 | 45 | 25 | 100 | 120 | 90 |
| 526 (pSUP487) | 4 × $10^6$ | 4 × $10^6$ | 2 × $10^6$ | 73 | 70 | 28 | 40 | 38 | 7 |

[a]Colony forming units; mean of 4 replicas

The stability of the Bt CP gene containing construct pSUP487 in *Pseudomonas cepacia* 526 was further examined by determining the loss of plasmid drug resistance marker chloramphenicol in liquid culture in the absence of selective pressure Test cultures including *P. cepacia* 526 and the *P. cepacia* 526 transconjugants containing pSUP487 and pSUP204 were grown overnight in Luria broth with appropriate antibiotics (100 μg/ml rif; 50 μg/ml cam). Fresh Luria broth cultures were then inoculated from each of the overnight cultures of the test strains so that the initial inoculum level was about 100 bacteria/ml. These cultures were grown to stationary phase (about 24 hr) at 28° C. in the absence of antibiotics, after which viable cell counts on nutrient agar plates with appropriate antibiotic were determined. This growth period represented approximately 20–24 generations. The pSUP487 plasmid proved to be relatively unstable being retained in only 5.3% of the total *P. cepacia* 526 compared to the parent pSUP204 plasmid which was retained in 97% of the *P. cepacia* 526 over this time period.

EXAMPLE 6

Protection of tobacco leaves by *P. cepacia* 526 (pSUP487) and *P. cepacia* 526 (pSKP/Bt)

The insecticidal activity of the *P. cepacia* 526 pSUP487 and pSKP/Bt transconjugants and their plant protection ability were examined by spraying bacterial cultures on tobacco leaves. These and all experiments using *P. cepacia* 526 transconjugants were performed so that release of the organisms to the environment was prevented. Test bacterial samples were prepared as in diet assays (vide supra). PBS bacterial cultures contained from about $1\text{-}5\times10^8$ bacteria/ml. Excised tobacco leaves from young plants that had been grown in growth chambers were sprayed with about 200 μl samples of either *P. cepacia* 526 pSUP487 or pSKP/Bt transformants or *P. cepacia* 526, *P. cepacia* 526 (pSUP204) or PBS controls. Treated leaves were allowed to dry and then placed in petri dishes on moistened filter paper (one leaf/dish). Five THW neonate larvae were then placed on each treated leaf. Four leaves were treated with each bacterial sample. After three days, leaves were scored for protection and death of larvae. As shown in Table 7, the samples of *P. cepacia* 526 containing the plasmids pSUP487 and pSKP/Bt were toxic to the larvae, while the controls were not. Furthermore, all leaves treated with these transconjugant strains were protected from the larvae, while the control leaves were devoured.

TABLE 7

Excised Leaf Protection; and Insect Mortality; Leaf Spray Experiment

| *P. cepacia* Strain | THW Larvae Mortality (no. alive/total)[a] |
|---|---|
| PBS | 20/20 |
| 526 | 20/20 |
| 526 (pSUP204) | 20/20 |
| 526 (pSUP487) | 2/20 |
| 526 (pSKP/Bt) | 5/20 |

[a]5 THW larvae/leaf, 4 leaves/treatment

EXAMPLE 7

Protection of tobacco plants by *P. cepacia* 526 pSUP487 and pSKP/Bt transconjugants Test bacterial samples were prepared as in diet assays (vide supra), except that PBS bacterial samples contained from about $1\text{-}5\times10^{10}$ bacteria/ml. Tobacco plants (*Nicotiana tabacum* var. Kentucky 17) were propagated from nodal sections in MS medium without hormone supplements (Murashige and Skoog (1962) Physiol. Plant. 15:473) in Magenta boxes under sterile conditions. After plants had rooted, they were removed from their boxes, sprayed with about 1 ml of bacterial test sample and returned to their boxes. Ten THW larvae were place on each test plant. Four replicas of each treatment were prepared. Treatments included the *P. cepacia* 526 pSUP487 and pSKP/Bt transconjugants and *P. cepacia* 526 and *P. cepacia* 526 (pSUP204) controls.

On the third day after inoculation, leaf samples were taken to assay colonization and plasmid retention. Samples were weighed and placed in 10 ml of PBS which contained 0.1% peptone. These leaf samples were shaken at room temperature for two hours, after which appropriate dilutions were plated on nutrient agar without antibiotics, with antibiotics either 100 μg/ml rif or 100 μg/ml rif +50μg/ml cam. All plates contained 150 μg/ml cycloheximide. Plates were incubated at 28° C. for 24–36 hours and counted. The leaf/PBS sample was considered as the 10× dilution. Results of colonization and plasmid stability assays are given in Table 8.

TABLE 8

Tobacco Plant Colonization; Spray Treatment Colonization and Plasmid Stability

| *P. cepacia* Strain | CFU/ml[a] | Bacterial Leaf Population 3 days Post-Inoculation[b] NA | NA(rif) | NA(rif + cam) | Ave. wt. of Leaf Samples (gm) | % Colonization | % Plasmid Stability |
|---|---|---|---|---|---|---|---|
| 526 | $2\times10^{10}$ | $5.2\times10^8$ | $5.6\times10^8$ | $2\times10^3$ | .86 | 107 | — |
| 526 (pSUP204) | $1.9\times10^{10}$ | $3.6\times10^8$ | $3.5\times10^8$ | $3.9\times10^8$ | .85 | 97 | 111 |
| 526 (pSUP487) | $5.9\times10^{10}$ | $4.8\times10^8$ | $4.7\times10^8$ | $3.9\times10^6$ | .88 | 97 | 0.83 |
| 526 (pSKF/BT) | $1.6\times10^{10}$ | $4\times10^8$ | $3.8\times10^8$ | $3.7\times10^8$ | .83 | 95 | 97 |

[a]Bacterial counts in undiluted test sample
[b]CFU/ml, mean of 4 replicas

On the sixth day after inoculation, larvae were recovered from each test plant box. Larvae were weighed and mortality was recorded. The results of this experiment are given in Table 9. Treatment with *P. cepacia* 526 (pSUP487) and *P. cepacia* 526 (pSKP/Bt) induced significant larvae mortality compared to controls. The average weight of larvae which remained alive on *P. cepacia* 526 (pSKP/Bt) treated plants was significantly lower than in controls.

It was noted that stability of pSKP/Bt plasmid was significantly higher, in this experiment, than expected based on previous experiments. Insect toxicity of 526 strains containing pSKP/Bt is also lower than expected. It is believed that a spontaneous deletion of part of the CP sequences in the pSKP/Bt has occurred in this experiment.

TABLE 9

Tobacco Plant Protection; Spray Treatment

| *P. cepacia* Strain | THW Larval Mortality No. Alive/Total[a] | Average Larval Wt. (mg) |
|---|---|---|
| 526 | 37/38 | 16.5 |
| 526 (pSUP204) | 39/39 | 17.5 |
| 526 (pSUP487) | 0/40 | ND[b] |

TABLE 9-continued

| Tobacco Plant Protection: Spray Treatment | | |
|---|---|---|
| | THW Larval Mortality | |
| *P. cepacia* Strain | No. Alive/Total[a] | Average Larval Wt. (mg) |
| 526 (pSKP/Bt) | 19/39 | 7.3 |

[a]For some treatments, not all larvae were recovered from boxes.
[b]ND = not determined.

EXAMPLE 8

Integration of Bt CP gene sequences into the *P. cepacia* 526 chromosome

The following represents an example of one way in which CP gene sequences can be stably integrated into the *P. cepacia* 526 chromosome via homologous recombination.

It is first important to identify chromosomal sequences in *P. cepacia* 526 that are not essential to the growth or other desirable properties, for example colonizing ability, of the strain. It is into these locations in the chromosome that the CP sequences can be inserted without affecting desired properties. One way in which potential insertion sites can be identified is by use of transposon mutagenesis. Transposon Tn5 insertions into the chromosome of *P. cepacia* 526 can be obtained using the suicide vector pSUP1011 (Simon et al. (1983) Biotechnology 9:784–791). *P. cepacia* 526 is mated with *E. coli* SM10 which carries vector pSUP1011 and selection is made for kanamycin resistant *P. cepacia* 526 which must carry Tn5 insertions, designated *P. cepacia* 526::Tn5. It is preferred to do this selection using minimal medium to exclude auxotrophic mutants. These Tn5 insertions are then screened using Eckhardt gels (Eckhardt (1978) Plasmid 1:584–585) to distinguish those mutants with chromosomal Tn5 insertions. The Tn5 chromosomal insertion mutants are then screened in colonization assays (as in Example 5) to select mutants unaffected in colonization. The location of Tn5 in these mutants represent potential sites for insertion of CP sequences.

The location of Tn5 insertions are then mapped and the CP sequences are inserted in their vicinity. These steps are achieved by preparing genomic libraries of both *P. cepacia* 526 and of *P. cepacia* 526::Tn5 (chromosome insert). Genomic libraries of these strains can be prepared, for exampie, by partial digestion of genomic DNA with a restriction enzyme such as Sau3A. It is preferred that the digestion conditions be adjusted so that the resultant fragments are in the 30 kb range, to facilitate DNA packaging. The digested DNA is then cloned into an appropriate vector, such as into the BamHI site of the cosmid pSUP205 (Simon et al., 1983), the ligation mix is introduced into an appropriate strain, like *E. coli* HB101, and transformants having the appropriate antibiotic markers chloramphen resistant, tetracycline-sensitive with pSUP205) are selected. The choice of vector in the preparation of the library of the Tn5 mutant strain is not critical; however, the use of a plasmid that will act as a suicide shuttle vector in the preparation of the library of the wild-type strain is preferred. The *P. cepacia* 526::Tn5 mutant strain clone library is then screened using hybridization techniques with a Tn5-labelled probe to identify clones containing Tn5 sequences, thereby identifying regions of the chromosome into which CP gene constructions can be inserted. Inserts in these Tn5 containing clones are then used as probes in similar hybridization experiments to identify clones from the wild-type library which contain the analogous genomic sequences and map the chromosome region of interest. It is into these regions of the chromosome that the CP gene constructs will be inserted. Once a restriction enzyme map of the cloned genomic region of interest is obtained, a convenient cloning site, usually a unique restriction enzyme site, is chosen for introduction of the CP sequences. The 5.1 SphI fragment (example 1.2, FIG. 2) which contains the HD73-like gene from *B. thuringiensis* HD-1 Dipel and its homologous promoter sequences or the approximately 8.3 kb HindIII-BamHI fragment from pSKP/Bt containing the HD73 CP gene chimaera in which the structural gene is under the control of the nptII gene promoter can be used as sources of CP gene sequences for introduction into the *P. cepacia* 526 genome. In order to follow the recombination event that will integrate the cloned CP sequences into the chromosome, a marker gene (for example, encoding an antibiotic resistance) must also be introduced into the genomic clone along with and closely-linked to the introduced CP sequences. It is also required that sufficient wild-type genomic sequences flanking (1 kb on either side is usually sufficient) the introduced CP and marker sequences remain to drive recombination. The suicide shuttle vector pSUP205 derivative that contains the genomic clone of interest into which the CP construct and marker gene are incorporated is then introduced into an appropriate carrier strain (for example, *E. coli* HB101) and the suicide vector derivative is mated into *P. cepacia* . The double recombination event that results in integration of the CP and marker sequences into the *P. cepacia* 526 chromosome is selected by screening for *P. cepacia* 526 which have the CP-linked marker phenotype and which have lost the marker phenotype of the shuttle vector (chloramphenicol-resistance with pSUP205). It is desirable to confirm that the desired sequences have been incorporated in the resultant *P. cepacia* 526 selections using restriction analysis of genomic DNA followed by Southern blotting using radiolabelled CP sequence as a hybridization probe. It is also desirable to assay plant colonization ability and insect toxicity of any confirmed selections.

Those skilled in the art will appreciate that the invention described herein and the methods of isolation and identification specifically described are susceptible to variations and modifications other than as specifically described. It is to be understood that the invention includes all such variations and modifications which fall within its spirit and scope.

We claim:

1. A genetically altered strain of *Pseudomonas cepacia* type Wisconsin which strain colonizes plant roots or leaves, said strain being genetically altered by introduction of a cloned insect toxic protein gene or partial protoxin gene of a strain of *Bacillus thuringiensis* such that said strain of *Pseudomonas cepacia* type Wisconsin is thereby rendered toxic to insects.

2. The genetically altered strain of *Pseudomonas cepacia* type Wisconsin of claim 1 wherein said insect toxic protein gene or partial protoxin gene is carried on a plasmid.

3. The genetically altered strain of *Pseudomonas cepacia* type Wisconsin of claim 1 wherein said insect toxic protein gene or partial protoxin gene is integrated into the chromosome of said strain.

4. The genetically altered strain of *Pseudomonas cepacia* type Wisconsin of claim 1 wherein said strain is obtained by genetic alteration of *Pseudomonas cepacia* 526.

5. The genetically altered strain of *Pseudomonas cepacia* type Wisconsin of claim 1 wherein said strain is obtained by genetic alteration of *Pseudomonas cepacia* 406.

6. A genetically altered strain of *Pseudomonas cepacia* type Wisconsin, which strain colonizes plant roots or leaves, said strain being genetically altered by the introduction of an insect toxic protein gene or partial protoxin gene of a strain of *Bacillus thuringiensis* such that said string of *Pseudomanas cepacia* type Wisconsin expresses said insect toxic protein gene or partial protoxin gene, and is thereby rendered toxic to insects, wherein said genetically altered insect toxic strain is *Pseudomonas cepacia* 526 (pSUP487).

7. A genetically altered strain of *Pseudomonas cepacia* type Wisconsin, which strain colonizes plant roots or leaves, said strain being genetically altered by the introduction of an insect toxic protein gene or partial protoxin gene of a string of *Bacillus thuringiensis* such that said strain of *Pseudomonas cepacia* type Wisconsin expresses said insect toxic protein gene or partial protoxin gene, and is thereby rendered toxic to insects, wherein said genetically altered insect toxic strain is *Pseudomonas cepacia* 526 (pSKP/Bt).

8. The genetically altered strain of claim 1 wherein said strain is genetically altered by the introduction of an insect toxic protein gene, which insect toxic protein gene is the crystal protein gene of *Bacillus thuringiensis* var. *kurstaki* HD-73.

9. The genetically altered strain of claim 1 wherein said strain is genetically altered by the introduction of an insect toxic protein gene, which insect toxic protein gene is the HD-73 like crystal protein gene of *Bacillus thuringiensis* var. *kurstaki* HD-1-Dipel.

10. The genetically altered strain of claim 1 wherein said strain is genetically altered by the introduction of an insect toxic protein gene, which insect toxic partial protoxin gene is the partial protoxin HD-73 gene of *Bacillus thuringiensis* var. *kurstaki* HD-73.

11. The genetically altered strain of claim 1 wherein said strain is genetically altered by the introduction of an insect toxic protein gene, which insect toxic partial protoxin gene is the partial protoxin HD-73-like gene of *Bacillus thuringiensis* var. *kurstaki* HD-1-Dipel.

12. An insecticidal plant protective composition which comprises (a) an insecticidally effective concentration of an insect toxic, non-phytopathogenic strain of *Pseudomonas cepacia* which colonizes roots or leaves of a plant, which strain has been genetically altered by the introduction of a cloned structural gene of a strain of *Bacillus thuringiensis*, which gene encodes a crystal protein or a partial protoxin and which gene is expressed by said *Pseudomonas cepacia*; and (b) an inert carrier.

13. An insecticidal plant protective composition which comprises p1 (a) an insecticidally effective concentration of an insect toxic strain of *Pseudomonas cepacia* type Wisconsin, which insect toxic strain has been produced by genetically altering a strain of *Pseudomonas cepacia* type Wisconsin by the introduction of a cloned *Bacillus thuringiensis* structural gene encoding an insect toxic crystal protein or a partial protoxin so that said structural gene is expressed by said strain of *Pseudomonas cepacia* type Wisconsin; and (b) an inert carrier.

14. The insecticidal plant protective composition of claim 13 wherein said insect toxic strain of *Pseudomonas cepacia* type Wisconsin is obtained by genetic alteration of *Pseudomonas cepacia* 526.

15. The insecticidal plant protective composition of claim 13 wherein said insect toxic strain of *Pseudomonas cepacia* is obtained by genetic alteration of *Pseudomonas cepacia* 406.

16. An insecticidal plant protective composition comprising an insecticidally effective concentration of the insect toxic strain of *Pseudomonas cepacia* type Wisconsin of claim 6 and an inert carrier.

17. An insecticidal plant protective composition comprising an insecticidally effective concentration of the insect toxic strain of *Pseudomonas cepacia* type Wisconsin of claim 7 and an inert carrier.

* * * * *

UNITED STATES PATENT AND TRADEMARK OFFICE

CERTIFICATE OF CORRECTION

PATENT NO. : 5,229,292

DATED : Jul. 20, 1993

INVENTOR(S) : Carolyn A. Stock; Thomas J. McLoughlin; Janet A. Klein; Michael J. Adang It is certified that error appears in the above-identified patent and that said Letters Patent is hereby corrected as shown below:

At column 1, line 56, please rewrite "(±1986)" as --(1986)--. At column 2, line 40, please rewrite "(pature ..." as --(pasture ...--. At column 2, line 57, please rewrite "Chirnomus" as --Chironomus--. At column 4, line 18, please rewrite "lead" as --leaf--. At column 4, line 40, please rewrite "*clepsos*" as --*clepsis*--. At column 4, line 42, please rewrite "(*Recrvaris*)" as --(*Recurvaria*)--. At column 6, line 52, please rewrite "vutworm)" as --cutworm--. At column 7, line 9, please rewrite "(omonvorous" as --omnivorous--. At column 7, line 26, please rewrite "leafworm")" as --armyworm--. At column 7, line 27, please rewrite "(Cotton" as --(Cotton leafworm)--. At column 7, line 32, please rewrite "*Sylleptederogata*" as --*Syllepte derogata*--. At column 9, line 5, please rewrite "Society of Microbiolgists" as --Society for Microbiology--. At column 9, line 51, please rewrite "*Organism*" as --*Organisms*--. At column 15, line 52, please rewrite "i&" as --if--. At column 21, line 57, please rewrite "BanHI" as --BamHI--.

At column 23, line 43, in Table 5, please rewrite "*capacia*" as --*cepacia*--. At column 23, line 48, please move the following from lines 58-61 to line 48, as a footnote to Table 5.:

UNITED STATES PATENT AND TRADEMARK OFFICE

CERTIFICATE OF CORRECTION

PATENT NO. 5,229,292

DATED Jul. 20, 1993

INVENTOR(S) Carolyn A. Stock; Thomas J. McLoughlin; Janet A. Klein; Michael J. Adang It is certified that error appears in the above-indentified patent and that said Letters Patent is hereby corrected as shown below:

[a]Bacterial counts in undiluted sample; CFU = colony forming units.
[b]ND = not done
[c]Those larvae alive were of reduced size compared to controls.
[d]Larvae either missing or killed by cap.

At column 24, line 49, please rewrite "Transconivgants" as --Transconjugants--. At column 27, line 56, please rewrite "chloramphen" as --(chloramphenicol--. At column 29, line 12, please rewrite "string" as --strain--. At column 29, line 21, please rewrite "string" as --strain--. At column 30, line 17, please delete "p1".

Signed and Sealed this

Thirtieth Day of May, 1995

Attest:

BRUCE LEHMAN

Attesting Officer

Commissioner of Patents and Trademarks